US006921646B2

(12) United States Patent
Scott et al.

(10) Patent No.: US 6,921,646 B2
(45) Date of Patent: Jul. 26, 2005

(54) PATCHED GENES AND USES RELATED THERETO

(75) Inventors: Matthew P. Scott, Stanford, CA (US); Lisa V. Goodrich, Palo Alto, CA (US); Ronald L. Johnson, Redwood City, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 09/754,032

(22) Filed: Jan. 3, 2001

(65) Prior Publication Data

US 2003/0148388 A1 Aug. 7, 2003

Related U.S. Application Data

(63) Continuation of application No. 08/954,668, filed on Oct. 20, 1997, now Pat. No. 6,172,200, which is a continuation of application No. 08/540,406, filed on Oct. 6, 1995, now Pat. No. 5,837,538, which is a continuation-in-part of application No. 08/319,745, filed on Oct. 7, 1994, now abandoned.

(51) Int. Cl.[7] ........................................... G01N 33/567
(52) U.S. Cl. ................ 435/7.21; 435/252.3; 435/320.1; 435/69.1; 436/501; 514/2; 530/350; 530/388.22; 536/23.5
(58) Field of Search ............................. 435/7.21, 69.1, 435/252.3, 320.1, 7.1; 436/501; 514/2; 530/350, 388.22; 536/23.5

(56) References Cited

U.S. PATENT DOCUMENTS

| 5,789,543 | A | * | 8/1998 | Ingham et al. | ............... 530/350 |
| 5,798,209 | A | | 8/1998 | Chan | .............................. 435/6 |
| 5,837,538 | A | | 11/1998 | Scott | ........................... 435/325 |
| 5,935,810 | A | | 8/1999 | Friedman et al. | .......... 435/69.1 |
| 6,027,882 | A | | 2/2000 | Scott et al. | |

FOREIGN PATENT DOCUMENTS

WO      WO9611260     4/1996      ............ C12N/5/00

OTHER PUBLICATIONS

Bowie et al., 1990, Science 247:1306–1310.*
Aguirre, A. et al, Biotecnologia Aplicada 13(1)32, 1996.*
Forbes–AJ et al., Development 1993 Supplement, pp. 115–124.*
Hammerschmidt, M. et al. Protein kinase A is a common negative regulator of Hedgegog signaling in the vertebrate embryo. *Genes & Development* 10, 647–658 (1996).
Noveen, A. et al. cAMP, an Activator of Protein Kinase A, Suppresses the Expression of Sonic Hedgehog. *Biochem. Biophys. Res. Comm.* 219, 180–185 (1996).
Altaba et al., Cell 90:193–196, 1997.
Fan et al., Cell 81(3): 457–465, May 5, 1995.
Krishnan et al., Science 278: 1947–1950, Dec. 12, 1997.
Muller et al., Development 127: 2999–3007, 2000.
Mullins, L.J. & Mullins, J.J. Transgenesis in the Rat and Larger Mammals. *J. Clin. Invest.* 98, S37–S40 (1996).
Ngo, J.T. et al. Computational Complexity, Protein Structure Prediction, and the Levinthal Paradox. *Peptide Hormones* 491–494 (1976).
Rudinger, J. Characteristics of the amino acids as components of a peptide hormone sequence. *Endocrinology* 5–7 (1972).
Seamark R.F. Progress and Emerging Problems in Livestock Transgenesis: a Summary Perspective. *Reprod. Fert. Dev.* 6, 653–657 (1994).
Wall, R.J. Transgenic Livestock: Progress and Prospects for the Future. *Theriogenology* 45, 57–68 (1996).
Akimaru, H. et al., "Drosophila CBP is a co–activator of cubitus interruptus in hedgehog signaling", Nature 386 (6626): 735–738 (1997).
Akiyama, H. et al., "Cloning of a mouse smoothened cDNA and expression patterns of hedgehog signaling molecules during chondrogenesis and cartilage differentiation in conal mouse EC cells, ATDC5", Biophys Res. Comm., 235(1): 142–147 (1997).
Alberts, eds., Molecular Biology of the Cell, G–10 (1994).
Alcedo, J. et al., "The Drosophila smoothened gene encodes a seven–pass membrane protein, a putative receptor for the hedgehog signal", Cell, 86 (2): 221–232 (1996).
Alcedo, J. and Noll, M., "Hedgehog and its patched–smoothened receptor complex: a novel signaling mechanism at the cell surface", Biol. Chem., 378 (7): 583–590 (1997).
Alexandre, C. et al., "Transcriptional activation of hedgehog target genes in Drosophila is mediated directly by the cutitus interrptus protein, a member of the GLI family of zinc finger DNA–binding proteins", Genes Dev., 19 (16): 2003–2013 (1996).
Bale, A., "Variable expressivity of patched mutations in flies and humans", Am. J. Human Genet., 60 (1): 10–12 (1997).
Bellusci, S. et al., "Involvement of Sonic hedgehog (Shh) in mouse embryonic lung growth and morphongenesis", Development, 124 (1): 53–63 (1997).

(Continued)

*Primary Examiner*—Elizabeth Kemmerer
*Assistant Examiner*—Michael Brannock
(74) *Attorney, Agent, or Firm*—Ropes & Gray LLP

(57) ABSTRACT

Invertebrate and vertebrate patched genes are provided, including the mouse and human patched genes, as well as methods for isolation of related genes, where the genes may be of different species or in the same family. Having the ability to regulate the expression of the patched gene, allows for the elucidation of embryonic development, cellular regulation associated with signal transduction by the patched gene, the identification of agonist and antagonist to signal transduction, identification of ligands for binding to patched, isolation of the ligands, and assaying for levels of transcription and expression of the patched gene.

4 Claims, 1 Drawing Sheet

OTHER PUBLICATIONS

Bhat, K. and Schedl, P., "Requirement for engrailed and invected genes reveals novel regulatory interactions between engrailed/invected, patched,, gooseberry and wingless during Drosophila neurogenesis", Development, 124 (9)L 1675–1688 (1997).

Bitgood, M. et al., "Sertoli cell signaling by Desert hedgehog regulates the male germline", Curr. Biol., 6(3): 298–304 (1996).

Bokor, P. et al., "The roles of hedgehog, wingless and lines in patterning the dorsal epidermis in Drosophila", Development, 122 (4): 1083–1092 (1996).

Bowie et al., "Deciphering the Message in Protein Sequences: Tolerance to Amino Acid Substitutions", Science 247: 1306–1310 (1990).

Cadigan, K. et al., "Localized expression of sloppy paired protein maintains the polarity of Drosophila parasegments", Genes Dev., 8 (8):899–913 (1994).

Chanut, F. and Heberlein, U., "Role of the morphogenetic furow in establishing polarity in the Drosophila eye", Development, 121 (12): 4085–1094 (1995).

Chavrier et al., "The complexity of the Rab and Rho GTP–binding protein subfamilies revealed by a PCR cloning approach", Gene 112: 261–264 (1992).

Chen, E. et al., "Compartmental organization of the Drosophila genital imaginal disks", Development, 124(1): 205–218 (1997).

Chen, Y. et al., "Dual roles for patched in sequestering and transducing Hedgehog", Cell, 87(3): 553–563 (1996).

Concordet, J. et al., "Spatial regulation of a zebrafish patched homoloogue reflects the roles of sonic hedgehog and protein kinase A in neural tube and somite patterning", Development, 122 (9): 2835–2846 (1996).

Dhawan et al., "Systematic Delivery of Human Growth Hormone by Injection of Genetically Engineered Myoblasts", Science 254: 1509–1512 (1991).

Dominguez, M. et al., "Sending and receiving the hedgehog signal: control by the Drosophila Gli protein cubitus interruptus", Science, 272 (5268): 1621–1625 (1996).

Echelard, Y. et al., "Sonic hedgehog, a member of a family of putative signaling molecules, is implicated in the regulation of CNS polarity", Cell, 75: 1417–1430 (1993).

Epps, J. et al., "*Oroshigane,* a new segment polarity gene of Drosophila melanogaster, functions in hedgehog signal transduction", Genetics 145 (4): 1041–1052 (1997).

Epstein, D. et al., "Antagonizing cAMP–dependent protein kinase A in the dorsal CNS activates a conserved Sonic hedgehog signaling pathway", Development, 122 (9): 2884–2894 (1996).

Forbes, A. et al., "The role of segment polarity genes during early oogenesis in Drosophila", Development, 122 (10): 33283–3294 (1996).

Gailani et al., "Developmental Genes and Cancer: Role of Patched in Basal Cell Carcinoma of the Skin", J. Nat. Canc. Inst. 89 (15): 1103–1109 (1997).

Gailani, M. et al., "The role of the human homologue of Drosophila patched in spradic basal cell carcinomas", Nat. Genet., 14(1): 78–81 (1996).

Gomez–Skarmeta, J.L. et al. "*Araucan* and *caupolican*.provide a link between compartment subdivisions and pattering of sensory organs and veins in the Drosophila wing", Genes Dev., 10 (22): 2935–1945 (1996).

Goodrich, L. et al., "Altered neural cell fates and medulloblastoma in mouse patched mutants", Science, 277 (5329): 1109–1113 (1997).

Goodrich, L. et al., "Conservation of the hedgehog/patched signaling pathway from flies to mice: induction of a mouse patched gene by Hedgehog", Genes Dev., 10 (3): 301–312 (1996).

Gorlin, R., "Nevoid basal–cell carcinoma syndrome", Medicine, 66: 98–113 (1987).

Grindley, J. et al., "Evidence for the involvement of the Gli gene family in embryonic mouse lung development", Dev. Biol., 188 (2): 337–348 (1997).

Habuchi, et al., "Detailed deletion mapping of chromosome 9q bladder cancer: evidence or two tumour suppressor loci", Oncogene, 11:1671–1674 (1995).

Hahn, H. et al., "A mammalian patched homolog is expressed in target issues of sonic hedgehog and maps to a region associated with development abnormalities", J. Biol. Chem., 271 (21): 12125–12128 (1996).

Heemskerk, J. et al., "Drosophila hedgehog acts a a morphogen in cellular patterning", Cell 76: 449–460 (1994).

Hepker, J. et al., "Drosophila cubitus interruptus forms a negative feedback loop with patched and regulates expression of Hedgehog target genes", Development, 124 (2): 549–558 (1997).

Hidalgo, A. and Ingham, P., "Cell patterning in the Drosophila segment: spatial regulation of the segment polarity gene patched", Development, 110: 291–301 (1990).

Hooper et al., "The Drosophila patched gene encodes a putative membrane protein required for segmental patterning", Cell 59: 751–765 (1989).

Hynes, M., et a., Control of cell pattern in the neural tube by zinc finger transcription factor and oncogene_Neuron 19(1): 1997).

Ingham, "*Hedgehog* points the way", Curr. Biol. 4: 347–350 (1994).

Ingham, P. et al., "Role of the Drosophila patched gene in positional signalling", Nature, 353: 184–187 (1991).

Ingham, P. et al., "Quantitative effects of hedgehog and decapentaplegic activity on the patterning of the Drosophila wing"Curr. Biol., 5 (4): 432–440 (1995).

Jensen, A. et al., "Expression of Sonic hedgehog and its putative role as a precursor cell mitogen in the developing mouse retina", Development, 124 (2): 363–371 (1997).

Jiang, J. et al., "Protein kinase A and hedgehog signaling in Drosophila limb development", Cell, 80 (4): 563–572 (1995).

Johnson, R. et al., "Patched overexpression alters wing disc size and pattern: transcriptional and post–transcriptional effects on hedgehog targets", Development, 121 (12): 4161–4170 (1995).

Johnson, R. et al., "Human homolog of patched, a candidate gene for the basal cell nevus syndrome", Science, 272 (5268): 1668–1671 (1996).

Kalderon, D., "Morphogenetic signalling. Responses to hedgehog", Curr. Biol., 5 (6): 2279–2289 (1995).

Kato, Nippon Yakurigaku Zasshi, Folia Pharmacologica Japonica 102 (3): AN 94010590.

Kojima, T. et al., "Induction of a mirror–image duplication of anterior wing structures by localized hedgehog expression in the anterior compartment of Drosophila melanogaster wing imaginal discs", Gene, 148 (2): 211–7 (1994).

Krauss, S. et al., "A functionally conserved homolog of the Drosophila segment polarity gene hh is expressed in tissues with polarizing activity in zebrafish embryos", Cell, 75: 1431–1444 (1993).

Lepage et al., "Signal transduction by cAMP–dependent protein kinase A in Drosophila limb patterning", Nature, 373 (6516): 711–715 (1995).

Li, W., et al., "Function of protein kinase A in hedgehog signal transduction and Drosophila imaginal disc development", Cell, 80 (4): 553–562 (1995).

Loftus, S., et al., "Murine model of Niemann–Pick C disease: mutation in a cholesterol homeostatis gene", Science, 277 (5323): 232–235 (1997).

Ma, C. et al., "The segment polarity gene hedgehog is required for progression of the morphogenic furrow in the developing Drosophila eye", Cell, 75 (5): 927–938 (1993).

Ma, C. et al., "Wingless and patched are negative regulators of the morphogenetic furrow and can effect tissue polarity in the developing Drosophila compound eye", Development, 121 (8): 2279–2289 (1995).

Ma et al., "Molecular Cloning and Characterization of rKlk10, a cDNA encoding T–Kininogenase from Rat Submandibular Gland and Kidney", Biochemistry 31: 10922–10928.

Marigo, V. et al., "Biochemical evidence that patched is the Hedgehog receptor", Nature, 384 (6605): 176–179 (1996).

Marigo, V. et al., "Conservation in hedgehog signaling: induction of a chicken patched homolog by Sonic hedgehog in the developing limb", Development, 122 (4): 1225–1233 (1996).

Marigo, V. et al., "Sonic hedgehog differentially regulates expression of GLI and GLI3 during limb development", Dev. Biol., 180 (1): 273–283 (1996).

Marigo, V. et al., "Regulation of patched by sonic hedgehog in the developing neural tube", Proc. Natl. Acad. Sci. USA, 93(18):9346–9351 (1996).

Nakamura, T. et al., "Induction of osteogenic differentiation by hedgehog proteins", Biochem. Biophys. Res. Comm., 237 (2): 465–469 (1997).

Nakano, Y. et al., "A protein with several possible membrane–spanning domains encoded by the drosophila segment polarity gene patched", Nature, 341: 508–513 (1989).

Nusse, R. "Patching up Hedgehog", Nature, 384 (6605): 119–120 (1996).

Oro, A. et al., "Basal cell carcinomas in mice overexressing sonic hedgehog", Science, 276(5313)L 817–821 (1997).

Pennisi, "Gene Linked to Commonest Cancer", Science 272: 1583–1584 (1996).

Perrimon et al., "Generating lineage–specific markers to study Drosophila development", Dev. Genet. 12:238–252 (1991).

Perrimon, N., "Serpentine proteins lither into the wingless and hedgehog fields", Cell, 86 (4): 513–516 (1996).

Phillips, R. et al., "The Drosophila segment polarity gene patched is involved in a position signalling mechanism in imaginal discs", Development, 110: 105–114 (1990).

Quinn, A. et al., "Chromosome 9 allele loss occurs in both basal and squamous cell carcinomas of the skin", J. Inves. Dermatology, 102: 300–303 (1994).

Quinn, A. et al., "Delineation of two distinct deleted regions on chromosome 9 in human non–melanoma skin cancers", Genes, Chromosomes & Cancers, 11:222–225 (1994).

Riddle, R. et al., "Sonic hedgehog mediates the polarizing activity of the ZPA", Cell, 75: 1401–1416 (1993).

Roelink, H. et al., "Floor plate and motor neuron induction by vhh–1, a vertebrate homolog of hedgehot expressed by the notochord", Cell, 76: 761–775 (1994).

Rogers, G. et al., "Patched gene mutation screening in patients with basal cell nevus syndrome using biodirectional dideoxy fingerprinting", J. Invest. Dermatol. Abstracts, 108(4): 598, # 364, (1997).

Roush, W., "Hedgehog's patterning call is patched through, smoothly", Science, 274 (5291): 1304–1305 (1996).

Sanicola, M. et al., "Drawing a stripe in Drosophila imaginal disks: negative regulation of decapentaplagic and patched expression by engrailed", Genetics, 139 (2): 745–756 (1995).

Schuske, K. et al., "Patched overexpression causes loss of wingless expression in Drosophila embryos", Dev. Biol., 164 (1): 300–301 (1994).

Shilo, B., "Tumor suppressors. Dispatches from patched", Nature, 382 (6587): 115–116 (1996).

Simcox, A. et al., "Imaginal discs can be recovered from culture embryos mutant for the segment–polarity genes engrailed, naked and patched but nor from wingless", Development 107: 715–722 (1989).

Sisson, J. et al., "Costal2, a novel kinesin–related protein in the Hedgehog signaling pathway", Cell, 90 (2): 235–245 (1997).

Smith et al., "Genes Transferred by Retroviral Vectors into Normal and Mutant Myoblasts in Primary Cultures Are Expressed in Myotubes", Mol. Cell. Biol. 3268–3271 (1990).

Spradling et al., "Transposition of Cloned P Elements into Drosophila Germ Line Chromosomes", Science 218: 341–347 (1982).

Stone, D. et al., "The tumor–suppressor gene patched encodes a candidate receptor for Sonic hedgehog", Nature, 384 (6605): 129–134 (1996).

Struhl, G. et al., "Hedgehog acts by distinct gradient and signal relay mechanisms to organize cell type d cell polarity in the Drosophila abdomen", Development, 124 (11): 2155–2165 (1997).

Strutt, D. et al., "Ommatidial polarity in the Drosophila eye is determined by the direction of furrow progression and local interactions", Development, 121 (12): 4247–4256 (1995).

Strutt, D. et al., "Regulation of furrow progression in the Drosophila eye by cAMP–dependent protein kinase A", Nature, 373 (6516): 705–709 (1995).

Tabata, T. et al., "The Drosophila hedgehog gene is expressed specifically in posterior compartment cells and is a target of engrailed regulation", Genes Dev., 6(12B): 2635–2645 (1992).

Tabata, T. et al., "Hedgehog is a signaling protein with a key role in patterning Drosophila imaginal discs", Cell, 76: 89–102 (1994).

Takabatake, T. et al., "Hedgehog and patched gene expression in adult ocular tissues", FEBS Letters, 410 (2–3): 485–489 (1997).

Thummel, C. et al., "Vectors for Drosopl ila P–element mediated transformation and tissue culture transfection", Gene, 74: 445–446 (1988).

Von Ohlen, T. et al.,, "Hedgehog signaling regulates transcription through cubitus interruptus, a sequence-specific DNA binding protein", Proc. Natl. Acad. Sci. USA, 94 (6): 2404–2409 (1997).

Vorechovsky, I. et al, "Somatic mutations in the human homologue of Drosophila patched in primitive neuroectodermal tumors", Oncogene, 15 (3): 361–366 (1997).

Vortkamp, A., et al., "Regulation of rate of cartilage differentiation by Indian hedgehog and PTH–related protein", Science, 273 (5275): 613–622 (1996).

Watson, J., Recombinant DNA, W. H. Freeman and Co., New York, 363, (1992).

Wicking, C. et al., "Fine genetic mapping of the gene for nevoid basal cell carcinoma syndrome", Genomics, 22: 505–511 (1994).

* cited by examiner

SEQUENCE LISTING (1) GENERAL INFORMATION:

(iii) NUMBER OF SEQUENCES: 19

(2) INFORMATION FOR SEQ ID NO: 1:

(i) SEQUENCE CHARACTERISTICS:
      (A) LENGTH: 736 base pairs
      (B) TYPE: nucleic acid
      (C) STRANDEDNESS: single -continued (D) TOPOLOGY: linear (ii) MOLECULE TYPE: DNA (genomic)

(xi) SEQUENCE DESCRIPTION: SEQ ID NO: 1:

| | | | | | |
|---|---|---|---|---|---|
| AACNNCNNTN | NATGGCACCC | CCNCCCAACC | TTTNNNCCNN | NTAANCAAAA | NNCCCCNTTT | 60 |
| NATACCCCCT | NTAANANTTT | TCCACCNNNC | NNAAANNCCN | CTGNANACNA | NGNAAANCCN | 120 |
| TTTTTNAACC | CCCCCCACCC | GGAATTCCNA | NTNNCCNCCC | CCAAATTACA | ACTCCAGNCC | 180 |
| AAAATTNANA | NAATTGGTCC | TAACCTAACC | NATNGTTGTT | ACGGTTTCCC | CCCCCAAATA | 240 |
| CATGCACTGG | CCCGAACACT | TGATCGTTGC | CGTTCCAATA | AGAATAAATC | TGGTCATATT | 300 |
| AAACAAGCCN | AAAGCTTTAC | AAACTGTTGT | ACAATTAATG | GGCGAACACG | AACTGTTCGA | 360 |
| ATTCTGGTCT | GGACATTACA | AAGTGCACCA | CATCGGATGG | AACCAGGAGA | AGGCCACAAC | 420 |
| CGTACTGAAC | GCCTGGCAGA | AGAAGTTCGC | ACAGGTTGGT | GGTTGGCGCA | AGGAGTAGAG | 480 |
| TGAATGGTGG | TAATTTTTGG | TTGTTCCAGG | AGGTGGATCG | TCTGACGAAG | AGCAAGAAGT | 540 |
| CGTCGAATTA | CATCTTCGTG | ACGTTCTCCA | CCGCCAATTT | GAACAAGATG | TTGAAGGAGG | 600 |
| CGTCGAANAC | GGACGTGGTG | AAGCTGGGGG | TGGTGCTGGG | GGTGGCGGCG | GTGTACGGGT | 660 |
| GGGTGGCCCA | GTCGGGGCTG | GCTGCCTTGG | GAGTGCTGGT | CTTNGCGNGC | TNCNATTCGC | 720 |
| CCTATAGTNA | GNCGTA | | | | | 736 |

(2) INFORMATION FOR SEQ ID NO: 2:

(i) SEQUENCE CHARACTERISTICS:
       (A) LENGTH: 107 amino acids
       (B) TYPE: amino acid
       (C) STRANDEDNESS: single
       (D) TOPOLOGY: linear (ii) MOLECULE TYPE: protein (xi) SEQUENCE DESCRIPTION: SEQ ID NO: 2:

Xaa Pro Pro Pro Asn Tyr Asn Ser Xaa Pro Lys Xaa Xaa Xaa Leu Val
1               5                   10                  15

Leu Thr Pro Xaa Val Val Thr Val Ser Pro Pro Lys Tyr Met His Trp
            20                  25                  30

Pro Glu His Leu Ile Val Ala Val Pro Ile Arg Ile Asn Leu Val Ile
        35                  40                  45

Leu Asn Lys Pro Lys Ala Leu Gln Thr Val Val Gln Leu Met Gly Glu
    50                  55                  60

His Glu Leu Phe Glu Phe Trp Ser Gly His Tyr Lys Val His His Ile
65                  70                  75                  80

Gly Trp Asn Gln Glu Lys Ala Thr Thr Val Leu Asn Ala Trp Gln Lys
                85                  90                  95

Lys Phe Ala Gln Val Gly Gly Trp Arg Lys Glu
            100                 105

(2) INFORMATION FOR SEQ ID NO: 3:

(i) SEQUENCE CHARACTERISTICS:
       (A) LENGTH: 5187 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO: 3:

```
GGGTCTGTCA CCCGGAGCCG GAGTCCCCGG CGGCCAGCAG CGTCCTCGCG AGCCGAGCGC      60
CCAGGCGCGC CCGGAGCCCG CGGCGGCGGC GGCAACATGG CCTCGGCTGG TAACGCCGCC     120
GGGGCCCTGG GCAGGCAGGC CGGCGGCGGG AGGCGCAGAC GGACCGGGGG ACCGCACCGC     180
GCCGCGCCGG ACCGGGACTA TCTGCACCGG CCCAGCTACT GCGACGCCGC CTTCGCTCTG     240
GAGCAGATTT CCAAGGGGAA GGCTACTGGC CGGAAAGCGC CGCTGTGGCT GAGAGCGAAG     300
TTTCAGAGAC TCTTATTTAA ACTGGGTTGT TACATTCAAA AGAACTGCGG CAAGTTTTTG     360
GTTGTGGGTC TCCTCATATT TGGGGCCTTC GCTGTGGGAT TAAAGGCAGC TAATCTCGAG     420
ACCAACGTGG AGGAGCTGTG GGTGGAAGTT GGTGGACGAG TGAGTCGAGA ATTAAATTAT     480
ACCCGTCAGA AGATAGGAGA AGAGGCTATG TTTAATCCTC AACTCATGAT ACAGACTCCA     540
AAAGAAGAAG GCGCTAATGT TCTGACCACA GAGGCTCTCC TGCAACACCT GGACTCAGCA     600
CTCCAGGCCA GTCGTGTGCA CGTCTACATG TATAACAGGC AATGGAAGTT GGAACATTTG     660
TGCTACAAAT CAGGGGAACT TATCACGGAG ACAGGTTACA TGGATCAGAT AATAGAATAC     720
CTTTACCCTT GCTTAATCAT TACACCTTTG GACTGCTTCT GGGAAGGGGC AAAGCTACAG     780
TCCGGGACAG CATACCTCCT AGGTAAGCCT CCTTTACGGT GGACAAACTT TGACCCCTTG     840
GAATTCCTAG AAGAGTTAAA GAAAATAAAC TACCAAGTGG ACAGCTGGGA GGAAATGCTG     900
AATAAAGCCG AAGTTGGCCA TGGGTACATG GACCGGCCTT GCCTCAACCC AGCCGACCCA     960
GATTGCCCTG CCACAGCCCC TAACAAAAAT TCAACCAAAC CTCTTGATGT GGCCCTTGTT    1020
TTGAATGGTG GATGTCAAGG TTTATCCAGG AAGTATATGC ATTGGCAGGA GGAGTTGATT    1080
GTGGGTGGTA CCGTCAAGAA TGCCACTGGA AAACTTGTCA GCGCTCACGC CCTGCAAACC    1140
ATGTTCCAGT TAATGACTCC CAAGCAAATG TATGAACACT TCAGGGGCTA CGACTATGTC    1200
TCTCACATCA ACTGGAATGA AGACAGGGCA GCCGCCATCC TGGAGGCCTG GCAGAGGACT    1260
TACGTGGAGG TGGTTCATCA AAGTGTCGCC CCAAACTCCA CTCAAAAGGT GCTTCCCTTC    1320
ACAACCACGA CCCTGGACGA CATCCTAAAA TCCTTCTCTG ATGTCAGTGT CATCCGAGTG    1380
GCCAGCGGCT ACCTACTGAT GCTTGCCTAT GCCTGTTTAA CCATGCTGCG CTGGGACTGC    1440
TCCAAGTCCC AGGGTGCCGT GGGGCTGGCT GGCGTCCTGT TGGTTGCGCT GTCAGTGGCT    1500
GCAGGATTGG GCCTCTGCTC CTTGATTGGC ATTTCTTTTA ATGCTGCGAC AACTCAGGTT    1560
TTGCCGTTTC TTGCTCTTGG TGTTGGTGTG GATGATGTCT TCCTCCTGGC CCATGCATTC    1620
AGTGAAACAG GACAGAATAA GAGGATTCCA TTTGAGGACA GGACTGGGGA GTGCCTCAAG    1680
CGCACCGGAG CCAGCGTGGC CCTCACCTCC ATCAGCAATG TCACCGCCTT CTTCATGGCC    1740
GCATTGATCC CTATCCCTGC CCTGCGAGCG TTCTCCCTCC AGGCTGCTGT GGTGGTGGTA    1800
TTCAATTTTG CTATGGTTCT GCTCATTTTT CCTGCAATTC TCAGCATGGA TTTATACAGA    1860
CGTGAGGACA GAAGATTGGA TATTTTCTGC TGTTTCACAA GCCCCTGTGT CAGCAGGGTG    1920
ATTCAAGTTG AGCCACAGGC CTACACAGAG CCTCACAGTA ACACCGGTA CAGCCCCCCA    1980
CCCCCATACA CCAGCCACAG CTTCGCCCAC GAAACCCATA TCACTATGCA GTCCACCGTT    2040
CAGCTCCGCA CAGAGTATGA CCCTCACACG CACGTGTACT ACACCACCGC CGAGCCACGC    2100
TCTGAGATCT CTGTACAGCC TGTTACCGTC ACCCAGGACA ACCTCAGCTG TCAGAGTCCC    2160
GAGAGCACCA GCTCTACCAG GGACCTGCTC TCCCAGTTCT CAGACTCCAG CCTCCACTGC    2220
CTCGAGCCCC CCTGCACCAA GTGGACACTC TCTTCGTTTG CAGAGAAGCA CTATGCTCCT    2280
TTCCTCCTGA AACCCAAAGC CAAGGTTGTG GTAATCCTTC TTTTCCTGGG CTTGCTGGGG    2340
GTCAGCCTTT ATGGGACCAC CCGAGTGAGA GACGGGCTGG ACCTCACGGA CATTGTTCCC    2400
```

```
CGGGAAACCA GAGAATATGA CTTCATAGCT GCCCAGTTCA AGTACTTCTC TTTCTACAAC    2460

ATGTATATAG TCACCCAGAA AGCAGACTAC CCGAATATCC AGCACCTACT TTACGACCTT    2520

CATAAGAGTT TCAGCAATGT GAAGTATGTC ATGCTGGAGG AGAACAAGCA ACTTCCCCAA    2580

ATGTGGCTGC ACTACTTTAG AGACTGGCTT CAAGGACTTC AGGATGCATT TGACAGTGAC    2640

TGGGAAACTG GGAGGATCAT GCCAAACAAT TATAAAAATG GATCAGATGA CGGGGTCCTC    2700

GCTTACAAAC TCCTGGTGCA GACTGGCAGC CGAGACAAGC CCATCGACAT TAGTCAGTTG    2760

ACTAAACAGC GTCTGGTAGA CGCAGATGGC ATCATTAATC CGAGCGCTTT CTACATCTAC    2820

CTGACCGCTT GGGTCAGCAA CGACCCTGTA GCTTACGCTG CCTCCCAGGC AACATCCGG    2880

CCTCACCGGC CGGAGTGGGT CCATGACAAA GCCGACTACA TGCCAGAGAC CAGGCTGAGA    2940

ATCCCAGCAG CAGAGCCCAT CGAGTACGCT CAGTTCCCTT CTACCTCAA CGGCCTACGA    3000

GACACCTCAG ACTTTGTGGA AGCCATAGAA AAAGTGAGAG TCATCTGTAA CAACTATACG    3060

AGCCTGGGAC TGTCCAGCTA CCCCAATGGC TACCCCTTCC TGTTCTGGGA GCAATACATC    3120

AGCCTGCGCC ACTGGCTGCT GCTATCCATC AGCGTGGTGC TGGCCTGCAC GTTTCTAGTG    3180

TGCGCAGTCT TCCTCCTGAA CCCCTGGACG GCCGGGATCA TTGTCATGGT CCTGGCTCTG    3240

ATGACCGTTG AGCTCTTTGG CATGATGGGC CTCATTGGGA TCAAGCTGAG TGCTGTGCCT    3300

GTGGTCATCC TGATTGCATC TGTTGGCATC GGAGTGGAGT TCACCGTCCA CGTGGCTTTG    3360

GCCTTTCTGA CAGCCATTGG GGACAAGAAC CACAGGGCTA TGCTCGCTCT GGAACACATG    3420

TTTGCTCCCG TTCTGGACGG TGCTGTGTCC ACTCTGCTGG GTGTACTGAT GCTTGCAGGG    3480

TCCGAATTTG ATTTCATTGT CAGATACTTC TTTGCCGTCC TGGCCATTCT CACCGTCTTG    3540

GGGGTTCTCA ATGGACTGGT TCTGCTGCCT GTCCTCTTAT CCTTCTTTGG ACCGTGTCCT    3600

GAGGTGTCTC CAGCCAATGG CCTAAACCGA CTGCCCACTC CTTCGCCTGA GCCGCCTCCA    3660

AGTGTCGTCC GGTTTGCCGT GCCTCCTGGT CACACGAACA ATGGGTCTGA TTCCTCCGAC    3720

TCGGAGTACA GCTCTCAGAC CACGGTGTCT GGCATCAGTG AGGAGCTCAG GCAATACGAA    3780

GCACAGCAGG GTGCCGGAGG CCCTGCCCAC CAAGTGATTG TGGAAGCCAC AGAAAACCCT    3840

GTCTTTGCCC GGTCCACTGT GGTCCATCCG GACTCCAGAC ATCAGCCTCC CTTGACCCCT    3900

CGGCAACAGC CCCACCTGGA CTCTGGCTCC TTGTCCCCTG GACGGCAAGG CCAGCAGCCT    3960

CGAAGGGATC CCCCTAGAGA AGGCTTGCGG CCACCCCCCT ACAGACCGCG CAGAGACGCT    4020

TTTGAAATTT CTACTGAAGG GCATTCTGGC CCTAGCAATA GGGACCGCTC AGGGCCCCGT    4080

GGGGCCCGTT CTCACAACCC TCGGAACCCA ACGTCCACCG CCATGGGCAG CTCTGTGCCC    4140

AGCTACTGCC AGCCCATCAC CACTGTGACG GCTTCTGCTT CGGTGACTGT TGCTGTGCAT    4200

CCCCCGCCTG GACCTGGGCG CAACCCCCGA GGGGGGCCCT GTCCAGGCTA TGAGAGCTAC    4260

CCTGAGACTG ATCACGGGGT ATTTGAGGAT CCTCATGTGC CTTTTCATGT CAGGTGTGAG    4320

AGGAGGGACT CAAAGGTGGA GGTCATAGAG CTACAGGACG TGGAATGTGA GGAGAGGCCG    4380

TGGGGGAGCA GCTCCAACTG AGGGTAATTA AAATCTGAAG CAAAGAGGCC AAAGATTGGA    4440

AAGCCCCGCC CCCACCTCTT TCCAGAACTG CTTGAAGAGA ACTGCTTGGA ATTATGGGAA    4500

GGCAGTTCAT TGTTACTGTA ACTGATTGTA TTATTKKGTG AAATATTTCT ATAAATATTT    4560

AARAGGTGTA CACATGTAAT ATACATGGAA ATGCTGTACA GTCTATTTCC TGGGGCCTCT    4620

CCACTCCTGC CCCAGAGTGG GGAGACCACA GGGGCCCTTT CCCCTGTGTA CATTGGTCTC    4680

TGTGCCACAA CCAAGCTTAA CTTAGTTTTA AAAAAAATCT CCCAGCATAT GTCGCTGCTG    4740
```

-continued

```
CTTAAATATT GTATAATTTA CTTGTATAAT TCTATGCAAA TATTGCTTAT GTAATAGGAT    4800

TATTTGTAAA GGTTTCTGTT TAAAATATTT TAAATTTGCA TATCACAACC CTGTGGTAGG    4860

ATGAATTGTT ACTGTTAACT TTTGAACACG CTATGCGTGG TAATTGTTTA ACGAGCAGAC    4920

ATGAAGAAAA CAGGTTAATC CCAGTGGCTT CTCTAGGGGT AGTTGTATAT GGTTCGCATG    4980

GGTGGATGTG TGTGTGCATG TGACTTTCCA ATGTACTGTA TTGTGGTTTG TTGTTGTTGT    5040

TGCTGTTGTT GTTCATTTTG GTGTTTTTGG TTGCTTTGTA TGATCTTAGC TCTGGCCTAG    5100

GTGGGCTGGG AAGGTCCAGG TCTTTTTCTG TCGTGATGCT GGTGGAAAGG TGACCCCAAT    5160

CATCTGTCCT ATTCTCTGGG ACTATTC                                         5187
```

(2) INFORMATION FOR SEQ ID NO: 4:

(i) SEQUENCE CHARACTERISTICS:
       (A) LENGTH: 1311 amino acids
       (B) TYPE: amino acid
       (C) STRANDEDNESS: single
       (D) TOPOLOGY: linear (ii) MOLECULE TYPE: protein (xi) SEQUENCE DESCRIPTION: SEQ ID NO: 4:

```
Met Val Ala Pro Asp Ser Glu Ala Pro Ser Asn Pro Arg Ile Thr Ala
1               5                   10                  15

Ala His Glu Ser Pro Cys Ala Thr Glu Ala Arg His Ser Ala Asp Leu
            20                  25                  30

Tyr Ile Arg Thr Ser Trp Val Asp Ala Leu Ala Leu Ser Glu Leu
        35                  40                  45

Glu Lys Gly Asn Ile Glu Gly Gly Arg Thr Ser Leu Trp Ile Arg Ala
50                  55                  60

Trp Leu Gln Glu Gln Leu Phe Ile Leu Gly Cys Phe Leu Gln Gly Asp
65                  70                  75                  80

Ala Gly Lys Val Leu Phe Val Ala Ile Leu Val Leu Ser Thr Phe Cys
                85                  90                  95

Val Gly Leu Lys Ser Ala Gln Ile His Thr Arg Val Asp Gln Leu Trp
            100                 105                 110

Val Gln Glu Gly Gly Arg Leu Glu Ala Glu Leu Lys Tyr Thr Ala Gln
        115                 120                 125

Ala Leu Gly Glu Ala Asp Ser Ser Thr His Gln Leu Val Ile Gln Thr
130                 135                 140

Ala Lys Asp Pro Asp Val Ser Leu Leu His Pro Gly Ala Leu Leu Glu
145                 150                 155                 160

His Leu Lys Val Val His Ala Ala Thr Arg Val Thr Val His Met Tyr
                165                 170                 175

Asp Ile Glu Trp Arg Leu Lys Asp Leu Cys Tyr Ser Pro Ser Ile Pro
            180                 185                 190

Asp Phe Glu Gly Tyr His His Ile Glu Ser Ile Ile Asp Asn Val Ile
        195                 200                 205

Pro Cys Ala Ile Ile Thr Pro Leu Asp Cys Phe Trp Glu Gly Ser Lys
210                 215                 220

Leu Leu Gly Pro Asp Tyr Pro Ile Tyr Val Pro His Leu Lys His Lys
225                 230                 235                 240

Leu Gln Trp Thr His Leu Asn Pro Leu Glu Val Val Glu Glu Val Lys
                245                 250                 255

Lys Leu Lys Phe Gln Phe Pro Leu Ser Thr Ile Glu Ala Tyr Met Lys
            260                 265                 270
```

-continued

```
Arg Ala Gly Ile Thr Ser Ala Tyr Met Lys Lys Pro Cys Leu Asp Pro
            275                 280                 285

Thr Asp Pro His Cys Pro Ala Thr Ala Pro Asn Lys Lys Ser Gly His
        290                 295                 300

Ile Pro Asp Val Ala Ala Glu Leu Ser His Gly Cys Tyr Gly Phe Ala
305                 310                 315                 320

Ala Ala Tyr Met His Trp Pro Glu Gln Leu Ile Val Gly Gly Ala Thr
                325                 330                 335

Arg Asn Ser Thr Ser Ala Leu Arg Lys Ala Arg Xaa Leu Gln Thr Val
            340                 345                 350

Val Gln Leu Met Gly Glu Arg Glu Met Tyr Glu Tyr Trp Ala Asp His
        355                 360                 365

Tyr Lys Val His Gln Ile Gly Trp Asn Gln Glu Lys Ala Ala Ala Val
    370                 375                 380

Leu Asp Ala Trp Gln Arg Lys Phe Ala Ala Glu Val Arg Lys Ile Thr
385                 390                 395                 400

Thr Ser Gly Ser Val Ser Ser Ala Tyr Ser Phe Tyr Pro Phe Ser Thr
                405                 410                 415

Ser Thr Leu Asn Asp Ile Leu Gly Lys Phe Ser Glu Val Ser Leu Lys
            420                 425                 430

Asn Ile Ile Leu Gly Tyr Met Phe Met Leu Ile Tyr Val Ala Val Thr
        435                 440                 445

Leu Ile Gln Trp Arg Asp Pro Ile Arg Ser Gln Ala Gly Val Gly Ile
    450                 455                 460

Ala Gly Val Leu Leu Leu Ser Ile Thr Val Ala Ala Gly Leu Gly Phe
465                 470                 475                 480

Cys Ala Leu Leu Gly Ile Pro Phe Asn Ala Ser Ser Thr Gln Ile Val
                485                 490                 495

Pro Phe Leu Ala Leu Gly Leu Gly Val Gln Asp Met Phe Leu Leu Thr
            500                 505                 510

His Thr Tyr Val Glu Gln Ala Gly Asp Val Pro Arg Glu Glu Arg Thr
        515                 520                 525

Gly Leu Val Leu Lys Lys Ser Gly Leu Ser Val Leu Leu Ala Ser Leu
    530                 535                 540

Cys Asn Val Met Ala Phe Leu Ala Ala Ala Leu Leu Pro Ile Pro Ala
545                 550                 555                 560

Phe Arg Val Phe Cys Leu Gln Ala Ala Ile Leu Leu Leu Phe Asn Leu
                565                 570                 575

Gly Ser Ile Leu Leu Val Phe Pro Ala Met Ile Ser Leu Asp Leu Arg
            580                 585                 590

Arg Arg Ser Ala Ala Arg Ala Asp Leu Leu Cys Cys Leu Met Pro Glu
        595                 600                 605

Ser Pro Leu Pro Lys Lys Ile Pro Glu Arg Ala Lys Thr Arg Lys
    610                 615                 620

Asn Asp Lys Thr His Arg Ile Asp Thr Thr Arg Gln Pro Leu Asp Pro
625                 630                 635                 640

Asp Val Ser Glu Asn Val Thr Lys Thr Cys Cys Leu Ser Val Ser Leu
                645                 650                 655

Thr Lys Trp Ala Lys Asn Gln Tyr Ala Pro Phe Ile Met Arg Pro Ala
            660                 665                 670

Val Lys Val Thr Ser Met Leu Ala Leu Ile Ala Val Ile Leu Thr Ser
        675                 680                 685
```

-continued

```
Val Trp Gly Ala Thr Lys Val Lys Asp Gly Leu Asp Leu Thr Asp Ile
690             695                 700
Val Pro Glu Asn Thr Asp Glu His Glu Phe Leu Ser Arg Gln Glu Lys
705                 710                 715                 720
Tyr Phe Gly Phe Tyr Asn Met Tyr Ala Val Thr Gln Gly Asn Phe Glu
                725                 730                 735
Tyr Pro Thr Asn Gln Lys Leu Leu Tyr Glu Tyr His Asp Gln Phe Val
                740                 745                 750
Arg Ile Pro Asn Ile Ile Lys Asn Asp Asn Gly Gly Leu Thr Lys Phe
            755                 760                 765
Trp Leu Ser Leu Phe Arg Asp Trp Leu Leu Asp Leu Gln Val Ala Phe
770                 775                 780
Asp Lys Glu Val Ala Ser Gly Cys Ile Thr Gln Glu Tyr Trp Cys Lys
785                 790                 795                 800
Asn Ala Ser Asp Glu Gly Ile Leu Ala Tyr Lys Leu Met Val Gln Thr
                805                 810                 815
Gly His Val Asp Asn Pro Ile Asp Lys Ser Leu Ile Thr Ala Gly His
                820                 825                 830
Arg Leu Val Asp Lys Asp Gly Ile Ile Asn Pro Lys Ala Phe Tyr Asn
            835                 840                 845
Tyr Leu Ser Ala Trp Ala Thr Asn Asp Ala Leu Ala Tyr Gly Ala Ser
850                 855                 860
Gln Gly Asn Leu Lys Pro Gln Pro Gln Arg Trp Ile His Ser Pro Glu
865                 870                 875                 880
Asp Val His Leu Glu Ile Lys Lys Ser Ser Pro Leu Ile Tyr Thr Gln
                885                 890                 895
Leu Pro Phe Tyr Leu Ser Gly Leu Ser Asp Thr Xaa Ser Ile Lys Thr
                900                 905                 910
Leu Ile Arg Ser Val Arg Asp Leu Cys Leu Lys Tyr Glu Ala Lys Gly
            915                 920                 925
Leu Pro Asn Phe Pro Ser Gly Ile Pro Phe Leu Phe Trp Glu Gln Tyr
930                 935                 940
Leu Tyr Leu Arg Thr Ser Leu Leu Leu Ala Leu Ala Cys Ala Leu Ala
945                 950                 955                 960
Ala Val Phe Ile Ala Val Met Val Leu Leu Asn Ala Trp Ala Ala
                965                 970                 975
Val Leu Val Thr Leu Ala Leu Ala Thr Leu Val Leu Gln Leu Leu Gly
                980                 985                 990
Val Met Ala Leu Leu Gly Val Lys Leu Ser Ala Met Pro Ala Val Leu
            995                 1000                1005
Leu Val Leu Ala Ile Gly Arg Gly Val His Phe Thr Val His Leu Cys
    1010                1015                1020
Leu Gly Phe Val Thr Ser Ile Gly Cys Lys Arg Arg Arg Ala Ser Leu
1025                1030                1035                1040
Ala Leu Glu Ser Val Leu Ala Pro Val His Gly Ala Leu Ala Ala
                1045                1050                1055
Ala Leu Ala Ala Ser Met Leu Ala Ala Ser Glu Cys Gly Phe Val Ala
        1060                1065                1070
Arg Leu Phe Leu Arg Leu Leu Asp Ile Val Phe Leu Gly Leu Ile
        1075                1080                1085
Asp Gly Leu Leu Phe Phe Pro Ile Val Leu Ser Ile Leu Gly Pro Ala
1090                1095                1100
Ala Glu Val Arg Pro Ile Glu His Pro Glu Arg Leu Ser Thr Pro Ser
```

```
                    1105              1110              1115              1120
      Pro Lys Cys Ser Pro Ile His Pro Arg Lys Ser Ser Ser Ser Gly
                     1125              1130              1135
      Gly Gly Asp Lys Ser Ser Arg Thr Ser Lys Ser Ala Pro Arg Pro Cys
                     1140              1145              1150
      Ala Pro Ser Leu Thr Thr Ile Thr Glu Glu Pro Ser Ser Trp His Ser
                     1155              1160              1165
      Ser Ala His Ser Val Gln Ser Ser Met Gln Ser Ile Val Val Gln Pro
                     1170              1175              1180
      Glu Val Val Val Glu Thr Thr Thr Tyr Asn Gly Ser Asp Ser Ala Ser
      1185              1190              1195              1200
      Gly Arg Ser Thr Pro Thr Lys Ser Ser His Gly Gly Ala Ile Thr Thr
                     1205              1210              1215
      Thr Lys Val Thr Ala Thr Ala Asn Ile Lys Val Glu Val Val Thr Pro
                     1220              1225              1230
      Ser Asp Arg Lys Ser Arg Arg Ser Tyr His Tyr Tyr Asp Arg Arg Arg
                     1235              1240              1245
      Asp Arg Asp Glu Asp Arg Asp Arg Asp Arg Glu Arg Asp Arg Asp Arg
                     1250              1255              1260
      Asp Arg Asp Arg Asp Arg Asp Arg Asp Arg Asp Arg Asp Arg Asp Arg
      1265              1270              1275              1280
      Glu Arg Ser Arg Glu Arg Asp Arg Arg Asp Arg Tyr Arg Asp Glu Arg
                     1285              1290              1295
      Asp His Arg Ala Ser Pro Arg Glu Lys Arg Gln Arg Phe Trp Thr
                     1300              1305              1310

(2) INFORMATION FOR SEQ ID NO: 5:

(i) SEQUENCE CHARACTERISTICS:
        (A) LENGTH: 4434 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 5:

CGAAACAAGA GAGCGAGTGA GAGTAGGGAG AGCGTCTGTG TTGTGTGTTG AGTGTCGCCC      60

ACGCACACAG GCGCAAAACA GTGCACACAG ACGCCCGCTG GGCAAGAGAG AGTGAGAGAG     120

AGAAACAGCG GCGCGCGCTC GCCTAATGAA GTTGTTGGCC TGGCTGGCGT GCCGCATCCA     180

CGAGATACAG ATACATCTCT CATGGACCGC GACAGCCTCC CACGCGTTCC GGACACACAC     240

GGCGATGTGG TCGATGAGAA ATTATTCTCG GATCTTTACA TACGCACCAG CTGGGTGGAC     300

GCCCAAGTGG CGCTCGATCA GATAGATAAG GGCAAAGCGC GTGGCAGCCG CACGGCGATC     360

TATCTGCGAT CAGTATTCCA GTCCCACCTC GAAACCCTCG GCAGCTCCGT GCAAAAGCAC     420

GCGGGCAAGG TGCTATTCGT GGCTATCCTG GTGCTGAGCA CCTTCTGCGT CGGCCTGAAG     480

AGCGCCCAGA TCCACTCCAA GGTGCACCAG CTGTGGATCC AGGAGGGCGG CCGGCTGGAG     540

GCGGAACTGG CCTACACACA GAAGACGATC GGCGAGGACG AGTCGGCCAC GCATCAGCTG     600

CTCATTCAGA CGACCCACGA CCCGAACGCC TCCGTCCTGC ATCCGCAGGC GCTGCTTGCC     660

CACCTGGAGG TCCTGGTCAA GGCCACCGCC GTCAAGGTGC ACCTCTACGA CACCGAATGG     720

GGGCTGCGCG ACATGTGCAA CATGCCGAGC ACGCCCTCCT TCGAGGGCAT CTACTACATC     780

GAGCAGATCC TGCGCCACCT CATTCCGTGC TCGATCATCA CGCCGCTGGA CTGTTTCTGG     840
```

-continued

| | |
|---|---|
| GAGGGAAGCC AGCTGTTGGG TCCGGAATCA GCGGTCGTTA TACCAGGCCT CAACCAACGA | 900 |
| CTCCTGTGGA CCACCCTGAA TCCCGCCTCT GTGATGCAGT ATATGAAACA AAAGATGTCC | 960 |
| GAGGAAAAGA TCAGCTTCGA CTTCGAGACC GTGGAGCAGT ACATGAAGCG TGCGGCCATT | 1020 |
| GGCAGTGGCT ACATGGAGAA GCCCTGCCTG AACCCACTGA ATCCCAATTG CCCGGACACG | 1080 |
| GCACCGAACA AGAACAGCAC CCAGCCGCCG GATGTGGGAG CCATCCTGTC CGGAGGCTGC | 1140 |
| TACGGTTATG CCGCGAAGCA CATGCACTGG CCGGAGGAGC TGATTGTGGG CGGACGGAAG | 1200 |
| AGGAACCGCA GCGGACACTT GAGGAAGGCC CAGGCCCTGC AGTCGGTGGT GCAGCTGATG | 1260 |
| ACCGAGAAGG AAATGTACGA CCAGTGGCAG GACAACTACA AGGTGCACCA TCTTGGATGG | 1320 |
| ACGCAGGAGA AGGCAGCGGA GGTTTTGAAC GCCTGGCAGC GCAACTTTTC GCGGGAGGTG | 1380 |
| GAACAGCTGC TACGTAAACA GTCGAGAATT GCCACCAACT ACGATATCTA CGTGTTCAGC | 1440 |
| TCGGCTGCAC TGGATGACAT CCTGGCCAAG TTCTCCCATC CCAGCGCCTT GTCCATTGTC | 1500 |
| ATCGGCGTGG CCGTCACCGT TTTGTATGCC TTTTGCACGC TCCTCCGCTG GAGGGACCCC | 1560 |
| GTCCGTGGCC AGAGCAGTGT GGGCGTGGCC GGAGTTCTGC TCATGTGCTT CAGTACCGCC | 1620 |
| GCCGGATTGG GATTGTCAGC CCTGCTCGGT ATCGTTTTCA ATGCGCTGAC CGCTGCCTAT | 1680 |
| GCGGAGAGCA ATCGGCGGGA GCAGACCAAG CTGATTCTCA AGAACGCCAG CACCCAGGTG | 1740 |
| GTTCCGTTTT TGGCCCTTGG TCTGGGCGTC GATCACATCT TCATAGTGGG ACCGAGCATC | 1800 |
| CTGTTCAGTG CCTGCAGCAC CGCAGGATCC TTCTTTGCGG CCGCCTTTAT TCCGGTGCCG | 1860 |
| GCTTTGAAGG TATTCTGTCT GCAGGCTGCC ATCGTAATGT GCTCCAATTT GGCAGCGGCT | 1920 |
| CTATTGGTTT TTCCGGCCAT GATTTCGTTG GATCTACGGA GACGTACCGC CGGCAGGGCG | 1980 |
| GACATCTTCT GCTGCTGTTT TCCGGTGTGG AAGGAACAGC CGAAGGTGGC ACCTCCGGTG | 2040 |
| CTGCCGCTGA ACAACAACAA CGGGCGCGGG GCCCGGCATC CGAAGAGCTG CAACAACAAC | 2100 |
| AGGGTGCCGC TGCCCGCCCA GAATCCTCTG CTGGAACAGA GGGCAGACAT CCCTGGGAGC | 2160 |
| AGTCACTCAC TGGCGTCCTT CTCCCTGGCA ACCTTCGCCT TCAGCACTA CACTCCCTTC | 2220 |
| CTCATGCGCA GCTGGGTGAA GTTCCTGACC GTTATGGGTT TCCTGGCGGC CCTCATATCC | 2280 |
| AGCTTGTATG CCTCCACGCG CCTTCAGGAT GGCCTGGACA TTATTGATCT GGTGCCCAAG | 2340 |
| GACAGCAACG AGCACAAGTT CCTGGATGCT CAAACTCGGC TCTTTGGCTT CTACAGCATG | 2400 |
| TATGCGGTTA CCCAGGGCAA CTTTGAATAT CCCACCCAGC AGCAGTTGCT CAGGGACTAC | 2460 |
| CATGATTCCT TTGTGCGGGT GCCACATGTG ATCAAGAATG ATAACGGTGG ACTGCCGGAC | 2520 |
| TTCTGGCTGC TGCTCTTCAG CGAGTGGCTG GGTAATCTGC AAAAGATATT CGACGAGGAA | 2580 |
| TACCGCGACG GACGGCTGAC CAAGGAGTGC TGGTTCCCAA ACGCCAGCAG CGATGCCATC | 2640 |
| CTGGCCTACA AGCTAATCGT GCAAACCGGC CATGTGGACA ACCCCGTGGA CAAGGAACTG | 2700 |
| GTGCTCACCA ATCGCCTGGT CAACAGCGAT GGCATCATCA ACCAACGCGC CTTCTACAAC | 2760 |
| TATCTGTCGG CATGGGCCAC CAACGACGTC TTCGCCTACG GAGCTTCTCA GGGCAAATTG | 2820 |
| TATCCGGAAC CGCGCCAGTA TTTTCACCAA CCCAACGAGT ACGATCTTAA GATACCCAAG | 2880 |
| AGTCTGCCAT TGGTCTACGC TCAGATGCCC TTTTACCTCC ACGGACTAAC AGATACCTCG | 2940 |
| CAGATCAAGA CCCTGATAGG TCATATTCGC GACCTGAGCG TCAAGTACGA GGGCTTCGGC | 3000 |
| CTGCCCAACT ATCCATCGGG CATTCCCTTC ATCTTCTGGG AGCAGTACAT GACCCTGCGC | 3060 |
| TCCTCACTGG CCATGATCCT GGCCTGCGTG CTACTCGCCG CCCTGGTGCT GGTCTCCCTG | 3120 |
| CTCCTGCTCT CCGTTTGGGC CGCCGTTCTC GTGATCCTCA GCGTTCTGGC CTCGCTGGCC | 3180 |
| CAGATCTTTG GGGCCATGAC TCTGCTGGGC ATCAAACTCT CGGCCATTCC GGCAGTCATA | 3240 |

-continued

```
CTCATCCTCA GCGTGGGCAT GATGCTGTGC TTCAATGTGC TGATATCACT GGGCTTCATG       3300

ACATCCGTTG CAACCGACA GCGCCGCGTC CAGCTGAGCA TGCAGATGTC CCTGGGACCA        3360

CTTGTCCACG GCATGCTGAC CTCCGGAGTG GCCGTGTTCA TGCTCTCCAC GTCGCCCTTT       3420

GAGTTTGTGA TCCGGCACTT CTGCTGGCTT CTGCTGGTGG TCTTATGCGT TGGCGCCTGC       3480

AACAGCCTTT TGGTGTTCCC CATCCTACTG AGCATGGTGG GACCGGAGGC GGAGCTGGTG       3540

CCGCTGGAGC ATCCAGACCG CATATCCACG CCCTCTCCGC TGCCCGTGCG CAGCAGCAAG       3600

AGATCGGGCA AATCCTATGT GGTGCAGGGA TCGCGATCCT CGCGAGGCAG CTGCCAGAAG       3660

TCGCATCACC ACCACCACAA AGACCTTAAT GATCCATCGC TGACGACGAT CACCGAGGAG       3720

CCGCAGTCGT GGAAGTCCAG CAACTCGTCC ATCCAGATGC CAATGATTG GACCTACCAG        3780

CCGCGGGAAC AGCGACCCGC CTCCTACGCG GCCCCGCCCC CCGCCTATCA CAAGGCCGCC       3840

GCCCAGCAGC ACCACCAGCA TCAGGGCCCG CCCACAACGC CCCGCCTCC CTTCCCGACG        3900

GCCTATCCGC CGGAGCTGCA GAGCATCGTG GTGCAGCCGG AGGTGACGGT GGAGACGACG       3960

CACTCGGACA GCAACACCAC CAAGGTGACG GCCACGGCCA ACATCAAGGT GGAGCTGGCC       4020

ATGCCCGGCA GGGCGGTGCG CAGCTATAAC TTTACGAGTT AGCACTAGCA CTAGTTCCTG       4080

TAGCTATTAG GACGTATCTT TAGACTCTAG CCTAAGCCGT AACCCTATTT GTATCTGTAA       4140

AATCGATTTG TCCAGCGGGT CTGCTGAGGA TTTCGTTCTC ATGGATTCTC ATGGATTCTC       4200

ATGGATGCTT AAATGGCATG GTAATTGGCA AAATATCAAT TTTTGTGTCT CAAAAGATG       4260

CATTAGCTTA TGGTTTCAAG ATACATTTTT AAAGAGTCCG CCAGATATTT ATATAAAAAA       4320

AATCCAAAAT CGACGTATCC ATGAAAATTG AAAAGCTAAG CAGACCCGTA TGTATGTATA       4380

TGTGTATGCA TGTTAGTTAA TTTCCCGAAG TCCGGTATTT ATAGCAGCTG CCTT            4434
```

(2) INFORMATION FOR SEQ ID NO: 6:

(i) SEQUENCE CHARACTERISTICS:
      (A) LENGTH: 1285 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO: 6:

```
Met Asp Arg Asp Ser Leu Pro Arg Val Pro Asp Thr His Gly Asp Val
1               5                   10                  15

Val Asp Glu Lys Leu Phe Ser Asp Leu Tyr Ile Arg Thr Ser Trp Val
                20                  25                  30

Asp Ala Gln Val Ala Leu Asp Gln Ile Asp Lys Gly Lys Ala Arg Gly
            35                  40                  45

Ser Arg Thr Ala Ile Tyr Leu Arg Ser Val Phe Gln Ser His Leu Glu
        50                  55                  60

Thr Leu Gly Ser Ser Val Gln Lys His Ala Gly Lys Val Leu Phe Val
65                  70                  75                  80

Ala Ile Leu Val Leu Ser Thr Phe Cys Val Gly Leu Lys Ser Ala Gln
                85                  90                  95

Ile His Ser Lys Val His Gln Leu Trp Ile Gln Glu Gly Gly Arg Leu
                100                 105                 110

Glu Ala Glu Leu Ala Tyr Thr Gln Lys Thr Ile Gly Glu Asp Glu Ser
            115                 120                 125

Ala Thr His Gln Leu Leu Ile Gln Thr Thr His Asp Pro Asn Ala Ser
```

-continued

```
                130                 135                 140
Val Leu His Pro Gln Ala Leu Leu Ala His Leu Glu Val Leu Val Lys
145                 150                 155                 160

Ala Thr Ala Val Lys Val His Leu Tyr Asp Thr Glu Trp Gly Leu Arg
                165                 170                 175

Asp Met Cys Asn Met Pro Ser Thr Pro Ser Phe Glu Gly Ile Tyr Tyr
                180                 185                 190

Ile Glu Gln Ile Leu Arg His Leu Ile Pro Cys Ser Ile Ile Thr Pro
                195                 200                 205

Leu Asp Cys Phe Trp Glu Gly Ser Gln Leu Leu Gly Pro Glu Ser Ala
210                 215                 220

Val Val Ile Pro Gly Leu Asn Gln Arg Leu Leu Trp Thr Thr Leu Asn
225                 230                 235                 240

Pro Ala Ser Val Met Gln Tyr Met Lys Gln Lys Met Ser Glu Glu Lys
                245                 250                 255

Ile Ser Phe Asp Phe Glu Thr Val Glu Gln Tyr Met Lys Arg Ala Ala
                260                 265                 270

Ile Gly Ser Gly Tyr Met Glu Lys Pro Cys Leu Asn Pro Leu Asn Pro
                275                 280                 285

Asn Cys Pro Asp Thr Ala Pro Asn Lys Asn Ser Thr Gln Pro Pro Asp
                290                 295                 300

Val Gly Ala Ile Leu Ser Gly Gly Cys Tyr Gly Tyr Ala Ala Lys His
305                 310                 315                 320

Met His Trp Pro Glu Glu Leu Ile Val Gly Gly Arg Lys Arg Asn Arg
                325                 330                 335

Ser Gly His Leu Arg Lys Ala Gln Ala Leu Gln Ser Val Val Gln Leu
                340                 345                 350

Met Thr Glu Lys Glu Met Tyr Asp Gln Trp Gln Asp Asn Tyr Lys Val
                355                 360                 365

His His Leu Gly Trp Thr Gln Glu Lys Ala Ala Glu Val Leu Asn Ala
                370                 375                 380

Trp Gln Arg Asn Phe Ser Arg Glu Val Glu Gln Leu Leu Arg Lys Gln
385                 390                 395                 400

Ser Arg Ile Ala Thr Asn Tyr Asp Ile Tyr Val Phe Ser Ser Ala Ala
                405                 410                 415

Leu Asp Asp Ile Leu Ala Lys Phe Ser His Pro Ser Ala Leu Ser Ile
                420                 425                 430

Val Ile Gly Val Ala Val Thr Val Leu Tyr Ala Phe Cys Thr Leu Leu
                435                 440                 445

Arg Trp Arg Asp Pro Val Arg Gly Gln Ser Ser Val Gly Val Ala Gly
450                 455                 460

Val Leu Leu Met Cys Phe Ser Thr Ala Ala Gly Leu Gly Leu Ser Ala
465                 470                 475                 480

Leu Leu Gly Ile Val Phe Asn Ala Leu Thr Ala Ala Tyr Ala Glu Ser
                485                 490                 495

Asn Arg Arg Glu Gln Thr Lys Leu Ile Leu Lys Asn Ala Ser Thr Gln
                500                 505                 510

Val Val Pro Phe Leu Ala Leu Gly Leu Gly Val Asp His Ile Phe Ile
                515                 520                 525

Val Gly Pro Ser Ile Leu Phe Ser Ala Cys Ser Thr Ala Gly Ser Phe
                530                 535                 540

Phe Ala Ala Ala Phe Ile Pro Val Pro Ala Leu Lys Val Phe Cys Leu
545                 550                 555                 560
```

-continued

```
Gln Ala Ala Ile Val Met Cys Ser Asn Leu Ala Ala Leu Leu Val
                565                 570                 575
Phe Pro Ala Met Ile Ser Leu Asp Leu Arg Arg Thr Ala Gly Arg
            580                 585                 590
Ala Asp Ile Phe Cys Cys Cys Phe Pro Val Trp Lys Glu Gln Pro Lys
        595                 600                 605
Val Ala Pro Pro Val Leu Pro Leu Asn Asn Asn Gly Arg Gly Ala
    610                 615                 620
Arg His Pro Lys Ser Cys Asn Asn Asn Arg Val Pro Leu Pro Ala Gln
625                 630                 635                 640
Asn Pro Leu Leu Glu Gln Arg Ala Asp Ile Pro Gly Ser Ser His Ser
                645                 650                 655
Leu Ala Ser Phe Ser Leu Ala Thr Phe Ala Phe Gln His Tyr Thr Pro
            660                 665                 670
Phe Leu Met Arg Ser Trp Val Lys Phe Leu Thr Val Met Gly Phe Leu
        675                 680                 685
Ala Ala Leu Ile Ser Ser Leu Tyr Ala Ser Thr Arg Leu Gln Asp Gly
    690                 695                 700
Leu Asp Ile Ile Asp Leu Val Pro Lys Asp Ser Asn Glu His Lys Phe
705                 710                 715                 720
Leu Asp Ala Gln Thr Arg Leu Phe Gly Phe Tyr Ser Met Tyr Ala Val
                725                 730                 735
Thr Gln Gly Asn Phe Glu Tyr Pro Thr Gln Gln Gln Leu Leu Arg Asp
            740                 745                 750
Tyr His Asp Ser Phe Arg Val Pro His Val Ile Lys Asn Asp Asn Gly
        755                 760                 765
Gly Leu Pro Asp Phe Trp Leu Leu Phe Ser Glu Trp Leu Gly Asn
    770                 775                 780
Leu Gln Lys Ile Phe Asp Glu Glu Tyr Arg Asp Gly Arg Leu Thr Lys
785                 790                 795                 800
Glu Cys Trp Phe Pro Asn Ala Ser Ser Asp Ala Ile Leu Ala Tyr Lys
                805                 810                 815
Leu Ile Val Gln Thr Gly His Val Asp Asn Pro Val Asp Lys Glu Leu
            820                 825                 830
Val Leu Thr Asn Arg Leu Val Asn Ser Asp Gly Ile Ile Asn Gln Arg
        835                 840                 845
Ala Phe Tyr Asn Tyr Leu Ser Ala Trp Ala Thr Asn Asp Val Phe Ala
    850                 855                 860
Tyr Gly Ala Ser Gln Gly Lys Leu Tyr Pro Glu Pro Arg Gln Tyr Phe
865                 870                 875                 880
His Gln Pro Asn Glu Tyr Asp Leu Lys Ile Pro Lys Ser Leu Pro Leu
                885                 890                 895
Val Tyr Ala Gln Met Pro Phe Tyr Leu His Gly Leu Thr Asp Thr Ser
            900                 905                 910
Gln Ile Lys Thr Leu Ile Gly His Ile Arg Asp Leu Ser Val Lys Tyr
        915                 920                 925
Glu Gly Phe Gly Leu Pro Asn Tyr Pro Ser Gly Ile Pro Phe Ile Phe
    930                 935                 940
Trp Glu Gln Tyr Met Thr Leu Arg Ser Ser Leu Ala Met Ile Leu Ala
945                 950                 955                 960
Cys Val Leu Leu Ala Ala Leu Val Leu Val Ser Leu Leu Leu Ser
                965                 970                 975
```

```
Val Trp Ala Ala Val Leu Val Ile Leu Ser Val Leu Ala Ser Leu Ala
            980                 985                 990

Gln Ile Phe Gly Ala Met Thr Leu Leu Gly Ile Lys Leu Ser Ala Ile
            995                1000                1005

Pro Ala Val Ile Leu Ile Leu Ser Val Gly Met Met Leu Cys Phe Asn
           1010                1015                1020

Val Leu Ile Ser Leu Gly Phe Met Thr Ser Val Gly Asn Arg Gln Arg
1025                1030                1035                1040

Arg Val Gln Leu Ser Met Gln Met Ser Leu Gly Pro Leu Val His Gly
               1045                1050                1055

Met Leu Thr Ser Gly Val Ala Val Phe Met Leu Ser Thr Ser Pro Phe
           1060                1065                1070

Glu Phe Val Ile Arg His Phe Cys Trp Leu Leu Leu Val Val Leu Cys
           1075                1080                1085

Val Gly Ala Cys Asn Ser Leu Leu Val Phe Pro Ile Leu Leu Ser Met
           1090                1095                1100

Val Gly Pro Glu Ala Glu Leu Val Pro Leu Glu His Pro Asp Arg Ile
1105                1110                1115                1120

Ser Thr Pro Ser Pro Leu Pro Val Arg Ser Ser Lys Arg Ser Gly Lys
               1125                1130                1135

Ser Tyr Val Val Gln Gly Ser Arg Ser Ser Arg Gly Ser Cys Gln Lys
           1140                1145                1150

Ser His His His His His Lys Asp Leu Asn Asp Pro Ser Leu Thr Thr
               1155                1160                1165

Ile Thr Glu Glu Pro Gln Ser Trp Lys Ser Ser Asn Ser Ser Ile Gln
           1170                1175                1180

Met Pro Asn Asp Trp Thr Tyr Gln Pro Arg Glu Gln Arg Pro Ala Ser
1185                1190                1195                1200

Tyr Ala Ala Pro Pro Pro Ala Tyr His Lys Ala Ala Ala Gln Gln His
               1205                1210                1215

His Gln His Gln Gly Pro Pro Thr Thr Pro Pro Pro Phe Pro Thr
           1220                1225                1230

Ala Tyr Pro Pro Glu Leu Gln Ser Ile Val Val Gln Pro Glu Val Thr
               1235                1240                1245

Val Glu Thr Thr His Ser Asp Ser Asn Thr Thr Lys Val Thr Ala Thr
           1250                1255                1260

Ala Asn Ile Lys Val Glu Leu Ala Met Pro Gly Arg Ala Val Arg Ser
1265                1270                1275                1280

Tyr Asn Phe Thr Ser
               1285

(2) INFORMATION FOR SEQ ID NO: 7:

(i) SEQUENCE CHARACTERISTICS:
        (A) LENGTH: 345 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 7:

AAGGTCCATC AGCTTTGGAT ACAGGAAGGT GGTTCGCTCG AGCATGAGCT AGCCTACACG        60

CAGAAATCGC TCGGCGAGAT GGACTCCTCC ACGCACCAGC TGCTAATCCA AACNCCCAAA       120

GATATGGACG CCTCGATACT GCACCCGAAC GCGCTACTGA CGCACCTGGA CGTGGTGAAG       180
```

| | |
|---|---|
| AAAGCGATCT CGGTGACGGT GCACATGTAC GACATCACGT GGAGNCTCAA GGACATGTGC | 240 |
| TACTCGCCCA GCATACCGAG NTTCGATACG CACTTTATCG AGCAGATCTT CGAGAACATC | 300 |
| ATACCGTGCG CGATCATCAC GCCGCTGGAT TGCTTTTGGG AGGGA | 345 |

(2) INFORMATION FOR SEQ ID NO: 8:

(i) SEQUENCE CHARACTERISTICS:
        (A) LENGTH: 115 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 8:

```
Lys Val His Gln Leu Trp Ile Gln Glu Gly Gly Ser Leu Glu His Glu
1               5                  10                  15

Leu Ala Tyr Thr Gln Lys Ser Leu Gly Glu Met Asp Ser Ser Thr His
            20                  25                  30

Gln Leu Leu Ile Gln Thr Pro Lys Asp Met Asp Ala Ser Ile Leu His
        35                  40                  45

Pro Asn Ala Leu Leu Thr His Leu Asp Val Val Lys Lys Ala Ile Ser
    50                  55                  60

Val Thr Val His Met Tyr Asp Ile Thr Trp Xaa Leu Lys Asp Met Cys
65                  70                  75                  80

Tyr Ser Pro Ser Ile Pro Xaa Phe Asp Thr His Phe Ile Glu Gln Ile
                85                  90                  95

Phe Glu Asn Ile Ile Pro Cys Ala Ile Ile Thr Pro Leu Asp Cys Phe
            100                 105                 110

Trp Glu Gly
        115
```

(2) INFORMATION FOR SEQ ID NO: 9:

(i) SEQUENCE CHARACTERISTICS:
        (A) LENGTH: 5187 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 9:

| | |
|---|---|
| GGGTCTGTCA CCCGGAGCCG GAGTCCCCGG CGGCCAGCAG CGTCCTCGCG AGCCGAGCGC | 60 |
| CCAGGCGCGC CCGGAGCCCG CGGCGGCGGC GGCAACATGG CCTCGGCTGG TAACGCCGCC | 120 |
| GGGGCCCTGG GCAGGCAGGC CGGCGGCGGG AGGCGCAGAC GGACCGGGGG ACCGCACCGC | 180 |
| GCCGCGCCGG ACCGGGACTA TCTGCACCGG CCCAGCTACT GCGACGCCGC CTTCGCTCTG | 240 |
| GAGCAGATTT CCAAGGGGAA GGCTACTGGC CGGAAAGCGC CGCTGTGGCT GAGAGCGAAG | 300 |
| TTTCAGAGAC TCTTATTTAA ACTGGGTTGT ACATTCAAA GAACTGCGG CAAGTTTTG | 360 |
| GTTGTGGGTC TCCTCATATT TGGGGCCTTC GCTGTGGGAT TAAAGGCAGC TAATCTCGAG | 420 |
| ACCAACGTGG AGGAGCTGTG GGTGGAAGTT GGTGGACGAG TGAGTCGAGA ATTAAATTAT | 480 |
| ACCCGTCAGA AGATAGGAGA GAGGCTATG TTTAATCCTC AACTCATGAT ACAGACTCCA | 540 |
| AAAGAAGAAG GCGCTAATGT TCTGACCACA GAGGCTCTCC TGCAACACCT GGACTCAGCA | 600 |
| CTCCAGGCCA GTCGTGTGCA CGTCTACATG TATAACAGGC AATGGAAGTT GGAACATTTG | 660 |
| TGCTACAAAT CAGGGGAACT TATCACGGAG ACAGGTTACA TGGATCAGAT AATAGAATAC | 720 |

```
CTTTACCCTT GCTTAATCAT TACACCTTTG GACTGCTTCT GGGAAGGGGC AAAGCTACAG      780

TCCGGGACAG CATACCTCCT AGGTAAGCCT CCTTTACGGT GGACAAACTT TGACCCCTTG      840

GAATTCCTAG AAGAGTTAAA GAAAATAAAC TACCAAGTGG ACAGCTGGGA GGAAATGCTG      900

AATAAAGCCG AAGTTGGCCA TGGGTACATG GACCGGCCTT GCCTCAACCC AGCCGACCCA      960

GATTGCCCTG CCACAGCCCC TAACAAAAAT TCAACCAAAC CTCTTGATGT GGCCCTTGTT     1020

TTGAATGGTG GATGTCAAGG TTTATCCAGG AAGTATATGC ATTGGCAGGA GGAGTTGATT     1080

GTGGGTGGTA CCGTCAAGAA TGCCACTGGA AAACTTGTCA GCGCTCACGC CCTGCAAACC     1140

ATGTTCCAGT TAATGACTCC CAAGCAAATG TATGAACACT TCAGGGGCTA CGACTATGTC     1200

TCTCACATCA ACTGGAATGA AGACAGGGCA GCCGCCATCC TGGAGGCCTG GCAGAGGACT     1260

TACGTGGAGG TGGTTCATCA AAGTGTCGCC CCAAACTCCA CTCAAAAGGT GCTTCCCTTC     1320

ACAACCACGA CCCTGGACGA CATCCTAAAA TCCTTCTCTG ATGTCAGTGT CATCCGAGTG     1380

GCCAGCGGCT ACCTACTGAT GCTTGCCTAT GCCTGTTTAA CCATGCTGCG CTGGGACTGC     1440

TCCAAGTCCC AGGGTGCCGT GGGGCTGGCT GGCGTCCTGT TGGTTGCGCT GTCAGTGGCT     1500

GCAGGATTGG GCCTCTGCTC CTTGATTGGC ATTTCTTTTA ATGCTGCGAC AACTCAGGTT     1560

TTGCCGTTTC TTGCTCTTGG TGTTGGTGTG GATGATGTCT TCCTCCTGGC CCATGCATTC     1620

AGTGAAACAG GACAGAATAA GAGGATTCCA TTTGAGGACA GGACTGGGGA GTGCCTCAAG     1680

CGCACCGGAG CCAGCGTGGC CCTCACCTCC ATCAGCAATG TCACCGCCTT CTTCATGGCC     1740

GCATTGATCC CTATCCCTGC CCTGCGAGCG TTCTCCCTCC AGGCTGCTGT GGTGGTGGTA     1800

TTCAATTTTG CTATGGTTCT GCTCATTTTT CCTGCAATTC TCAGCATGGA TTTATACAGA     1860

CGTGAGGACA GAAGATTGGA TATTTTCTGC TGTTTCACAA GCCCCTGTGT CAGCAGGGTG     1920

ATTCAAGTTG AGCCACAGGC CTACACAGAG CCTCACAGTA ACACCCGGTA CAGCCCCCCA     1980

CCCCCATACA CCAGCCACAG CTTCGCCCAC GAAACCCATA TCACTATGCA GTCCACCGTT     2040

CAGCTCCGCA CAGAGTATGA CCCTCACACG CACGTGTACT ACACCACCGC CGAGCCACGC     2100

TCTGAGATCT CTGTACAGCC TGTTACCGTC ACCCAGGACA ACCTCAGCTG TCAGAGTCCC     2160

GAGAGCACCA GCTCTACCAG GGACCTGCTC TCCCAGTTCT CAGACTCCAG CCTCCACTGC     2220

CTCGAGCCCC CCTGCACCAA GTGGACACTC TCTTCGTTTG CAGAGAAGCA CTATGCTCCT     2280

TTCCTCCTGA AACCCAAAGC CAAGGTTGTG GTAATCCTTC TTTTCCTGGG CTTGCTGGGG     2340

GTCAGCCTTT ATGGGACCAC CCGAGTGAGA GACGGGCTGG ACCTCACGGA CATTGTTCCC     2400

CGGGAAACCA GAGAATATGA CTTCATAGCT GCCCAGTTCA AGTACTTCTC TTTCTACAAC     2460

ATGTATATAG TCACCCAGAA AGCAGACTAC CCGAATATCC AGCACCTACT TTACGACCTT     2520

CATAAGAGTT TCAGCAATGT GAAGTATGTC ATGCTGGAGG AGAACAAGCA ACTTCCCCAA     2580

ATGTGGCTGC ACTACTTTAG AGACTGGCTT CAAGGACTTC AGGATGCATT TGACAGTGAC     2640

TGGGAAACTG GGAGGATCAT GCCAAACAAT TATAAAAATG GATCAGATGA CGGGGTCCTC     2700

GCTTACAAAC TCCTGGTGCA GACTGGCAGC CGAGACAAGC CATCGACAT TAGTCAGTTG     2760

ACTAAACAGC GTCTGGTAGA CGCAGATGGC ATCATTAATC CGAGCGCTTT CTACATCTAC     2820

CTGACCGCTT GGGTCAGCAA CGACCCTGTA GCTTACGCTG CCTCCCAGGC CAACATCCGG     2880

CCTCACCGGC CGGAGTGGGT CCATGACAAA GCCGACTACA TGCCAGAGAC CAGGCTGAGA     2940

ATCCCAGCAG CAGAGCCCAT CGAGTACGCT CAGTTCCCTT TCTACCTCAA CGGCCTACGA     3000

GACACCTCAG ACTTTGTGGA AGCCATAGAA AAAGTGAGAG TCATCTGTAA CAACTATACG     3060
```

```
AGCCTGGGAC TGTCCAGCTA CCCCAATGGC TACCCCTTCC TGTTCTGGGA GCAATACATC    3120

AGCCTGCGCC ACTGGCTGCT GCTATCCATC AGCGTGGTGC TGGCCTGCAC GTTTCTAGTG    3180

TGCGCAGTCT TCCTCCTGAA CCCCTGGACG GCCGGGATCA TTGTCATGGT CCTGGCTCTG    3240

ATGACCGTTG AGCTCTTTGG CATGATGGGC CTCATTGGGA TCAAGCTGAG TGCTGTGCCT    3300

GTGGTCATCC TGATTGCATC TGTTGGCATC GGAGTGGAGT TCACCGTCCA CGTGGCTTTG    3360

GCCTTTCTGA CAGCCATTGG GGACAAGAAC CACAGGGCTA TGCTCGCTCT GGAACACATG    3420

TTTGCTCCCG TTCTGGACGG TGCTGTGTCC ACTCTGCTGG GTGTACTGAT GCTTGCAGGG    3480

TCCGAATTTG ATTTCATTGT CAGATACTTC TTTGCCGTCC TGGCCATTCT CACCGTCTTG    3540

GGGGTTCTCA ATGGACTGGT TCTGCTGCCT GTCCTCTTAT CCTTCTTTGG ACCGTGTCCT    3600

GAGGTGTCTC CAGCCAATGG CCTAAACCGA CTGCCCACTC CTTCGCCTGA GCCGCCTCCA    3660

AGTGTCGTCC GGTTTGCCGT GCCTCCTGGT CACACGAACA ATGGGTCTGA TTCCTCCGAC    3720

TCGGAGTACA GCTCTCAGAC CACGGTGTCT GGCATCAGTG AGGAGCTCAG GCAATACGAA    3780

GCACAGCAGG GTGCCGGAGG CCCTGCCCAC CAAGTGATTG TGGAAGCCAC AGAAAACCCT    3840

GTCTTTGCCC GGTCCACTGT GGTCCATCCG GACTCCAGAC ATCAGCCTCC CTTGACCCCT    3900

CGGCAACAGC CCCACCTGGA CTCTGGCTCC TTGTCCCCTG GACGGCAAGG CCAGCAGCCT    3960

CGAAGGGATC CCCCTAGAGA AGGCTTGCGG CCACCCCCCT ACAGACCGCG CAGAGACGCT    4020

TTTGAAATTT CTACTGAAGG GCATTCTGGC CCTAGCAATA GGGACCGCTC AGGGCCCCGT    4080

GGGGCCCGTT CTCACAACCC TCGGAACCCA ACGTCCACCG CCATGGGCAG CTCTGTGCCC    4140

AGCTACTGCC AGCCCATCAC CACTGTGACG GCTTCTGCTT CGGTGACTGT TGCTGTGCAT    4200

CCCCCGCCTG GACCTGGGCG CAACCCCCGA GGGGGGCCCT GTCCAGGCTA TGAGAGCTAC    4260

CCTGAGACTG ATCACGGGGT ATTTGAGGAT CCTCATGTGC CTTTTCATGT CAGGTGTGAG    4320

AGGAGGGACT CAAAGGTGGA GGTCATAGAG CTACAGGACG TGGAATGTGA GGAGAGGCCG    4380

TGGGGGAGCA GCTCCAACTG AGGGTAATTA AAATCTGAAG CAAAGAGGCC AAAGATTGGA    4440

AAGCCCCGCC CCCACCTCTT TCCAGAACTG CTTGAAGAGA ACTGCTTGGA ATTATGGGAA    4500

GGCAGTTCAT TGTTACTGTA ACTGATTGTA TTATTKKGTG AAATATTTCT ATAAATATTT    4560

AARAGGTGTA CACATGTAAT ATACATGGAA ATGCTGTACA GTCTATTTCC TGGGGCCTCT    4620

CCACTCCTGC CCCAGAGTGG GGAGACCACA GGGGCCCTTT CCCCTGTGTA CATTGGTCTC    4680

TGTGCCACAA CCAAGCTTAA CTTAGTTTTA AAAAAAATCT CCCAGCATAT GTCGCTGCTG    4740

CTTAAATATT GTATAATTTA CTTGTATAAT TCTATGCAAA TATTGCTTAT GTAATAGGAT    4800

TATTTGTAAA GGTTTCTGTT TAAAATATTT TAAATTTGCA TATCACAACC CTGTGGTAGG    4860

ATGAATTGTT ACTGTTAACT TTTGAACACG CTATGCGTGG TAATTGTTTA ACGAGCAGAC    4920

ATGAAGAAAA CAGGTTAATC CCAGTGGCTT CTCTAGGGGT AGTTGTATAT GGTTCGCATG    4980

GGTGGATGTG TGTGTGCATG TGACTTTCCA ATGTACTGTA TTGTGGTTTG TTGTTGTTGT    5040

TGCTGTTGTT GTTCATTTTG GTGTTTTTGG TTGCTTTGTA TGATCTTAGC TCTGGCCTAG    5100

GTGGGCTGGG AAGGTCCAGG TCTTTTTCTG TCGTGATGCT GGTGGAAAGG TGACCCCAAT    5160

CATCTGTCCT ATTCTCTGGG ACTATTC                                       5187
```

(2) INFORMATION FOR SEQ ID NO: 10:

(i) SEQUENCE CHARACTERISTICS:
        (A) LENGTH: 1434 amino acids
        (B) TYPE: amino acid
        (C) STRANDEDNESS: single (D) TOPOLOGY: linear (ii) MOLECULE TYPE: protein (xi) SEQUENCE DESCRIPTION: SEQ ID NO: 10:

```
Met Ala Ser Ala Gly Asn Ala Ala Gly Ala Leu Gly Arg Gln Ala Gly
1               5                   10                  15

Gly Gly Arg Arg Arg Arg Thr Gly Gly Pro His Arg Ala Ala Pro Asp
            20                  25                  30

Arg Asp Tyr Leu His Arg Pro Ser Tyr Cys Asp Ala Ala Phe Ala Leu
        35                  40                  45

Glu Gln Ile Ser Lys Gly Lys Ala Thr Gly Arg Lys Ala Pro Leu Trp
50                  55                  60

Leu Arg Ala Lys Phe Gln Arg Leu Leu Phe Lys Leu Gly Cys Tyr Ile
65                  70                  75                  80

Gln Lys Asn Cys Gly Lys Phe Leu Val Val Gly Leu Leu Ile Phe Gly
                85                  90                  95

Ala Phe Ala Val Gly Leu Lys Ala Ala Asn Leu Glu Thr Asn Val Glu
            100                 105                 110

Glu Leu Trp Val Glu Val Gly Gly Arg Val Ser Arg Glu Leu Asn Tyr
        115                 120                 125

Thr Arg Gln Lys Ile Gly Glu Glu Ala Met Phe Asn Pro Gln Leu Met
130                 135                 140

Ile Gln Thr Pro Lys Glu Gly Ala Asn Val Leu Thr Thr Glu Ala
145                 150                 155                 160

Leu Leu Gln His Leu Asp Ser Ala Leu Gln Ala Ser Arg Val His Val
                165                 170                 175

Tyr Met Tyr Asn Arg Gln Trp Lys Leu Glu His Leu Cys Tyr Lys Ser
            180                 185                 190

Gly Glu Leu Ile Thr Glu Thr Gly Tyr Met Asp Gln Ile Ile Glu Tyr
        195                 200                 205

Leu Tyr Pro Cys Leu Ile Ile Thr Pro Leu Asp Cys Phe Trp Glu Gly
210                 215                 220

Ala Lys Leu Gln Ser Gly Thr Ala Tyr Leu Leu Gly Lys Pro Pro Leu
225                 230                 235                 240

Arg Trp Thr Asn Phe Asp Pro Leu Glu Phe Leu Glu Glu Leu Lys Lys
                245                 250                 255

Ile Asn Tyr Gln Val Asp Ser Trp Glu Glu Met Leu Asn Lys Ala Glu
            260                 265                 270

Val Gly His Gly Tyr Met Asp Arg Pro Cys Leu Asn Pro Ala Asp Pro
        275                 280                 285

Asp Cys Pro Ala Thr Ala Pro Asn Lys Asn Ser Thr Lys Pro Leu Asp
290                 295                 300

Val Ala Leu Val Leu Asn Gly Gly Cys Gln Gly Leu Ser Arg Lys Tyr
305                 310                 315                 320

Met His Trp Gln Glu Glu Leu Ile Val Gly Gly Thr Val Lys Asn Ala
                325                 330                 335

Thr Gly Lys Leu Val Ser Ala His Ala Leu Gln Thr Met Phe Gln Leu
            340                 345                 350

Met Thr Pro Lys Gln Met Tyr Glu His Phe Arg Gly Tyr Asp Tyr Val
        355                 360                 365

Ser His Ile Asn Trp Asn Glu Asp Arg Ala Ala Ala Ile Leu Glu Ala
370                 375                 380

Trp Gln Arg Thr Tyr Val Glu Val Val His Gln Ser Val Ala Pro Asn
```

-continued

```
            385                 390                 395                 400
Ser Thr Gln Lys Val Leu Pro Phe Thr Thr Thr Leu Asp Asp Ile
                405                 410                 415
Leu Lys Ser Phe Ser Asp Val Ser Val Ile Arg Val Ala Ser Gly Tyr
                420                 425                 430
Leu Leu Met Leu Ala Tyr Ala Cys Leu Thr Met Leu Arg Trp Asp Cys
                435                 440                 445
Ser Lys Ser Gln Gly Ala Val Gly Leu Ala Gly Val Leu Leu Val Ala
                450                 455                 460
Leu Ser Val Ala Ala Gly Leu Gly Leu Cys Ser Leu Ile Gly Ile Ser
465                 470                 475                 480
Phe Asn Ala Ala Thr Thr Gln Val Leu Pro Phe Leu Ala Leu Gly Val
                485                 490                 495
Gly Val Asp Asp Val Phe Leu Leu Ala His Ala Phe Ser Glu Thr Gly
                500                 505                 510
Gln Asn Lys Arg Ile Pro Phe Glu Asp Arg Thr Gly Glu Cys Leu Lys
                515                 520                 525
Arg Thr Gly Ala Ser Val Ala Leu Thr Ser Ile Ser Asn Val Thr Ala
                530                 535                 540
Phe Phe Met Ala Ala Leu Ile Pro Ile Pro Ala Leu Arg Ala Phe Ser
545                 550                 555                 560
Leu Gln Ala Ala Val Val Val Phe Asn Phe Ala Met Val Leu Leu
                565                 570                 575
Ile Phe Pro Ala Ile Leu Ser Met Asp Leu Tyr Arg Arg Glu Asp Arg
                580                 585                 590
Arg Leu Asp Ile Phe Cys Cys Phe Thr Ser Pro Cys Val Ser Arg Val
                595                 600                 605
Ile Gln Val Glu Pro Gln Ala Tyr Thr Glu Pro His Ser Asn Thr Arg
                610                 615                 620
Tyr Ser Pro Pro Pro Tyr Thr Ser His Ser Phe Ala His Glu Thr
625                 630                 635                 640
His Ile Thr Met Gln Ser Thr Val Gln Leu Arg Thr Glu Tyr Asp Pro
                645                 650                 655
His Thr His Val Tyr Tyr Thr Thr Ala Glu Pro Arg Ser Glu Ile Ser
                660                 665                 670
Val Gln Pro Val Thr Val Thr Gln Asp Asn Leu Ser Cys Gln Ser Pro
                675                 680                 685
Glu Ser Thr Ser Ser Thr Arg Asp Leu Leu Ser Gln Phe Ser Asp Ser
                690                 695                 700
Ser Leu His Cys Leu Glu Pro Pro Cys Thr Lys Trp Thr Leu Ser Ser
705                 710                 715                 720
Phe Ala Glu Lys His Tyr Ala Pro Phe Leu Leu Lys Pro Lys Ala Lys
                725                 730                 735
Val Val Val Ile Leu Leu Phe Leu Gly Leu Leu Gly Val Ser Leu Tyr
                740                 745                 750
Gly Thr Thr Arg Val Arg Asp Gly Leu Asp Leu Thr Asp Ile Val Pro
                755                 760                 765
Arg Glu Thr Arg Glu Tyr Asp Phe Ile Ala Ala Gln Phe Lys Tyr Phe
                770                 775                 780
Ser Phe Tyr Asn Met Tyr Ile Val Thr Gln Lys Ala Asp Tyr Pro Asn
785                 790                 795                 800
Ile Gln His Leu Leu Tyr Asp Leu His Lys Ser Phe Ser Asn Val Lys
                805                 810                 815
```

-continued

Tyr Val Met Leu Glu Glu Asn Lys Gln Leu Pro Gln Met Trp Leu His
        820                 825                 830

Tyr Phe Arg Asp Trp Leu Gln Gly Leu Gln Asp Ala Phe Asp Ser Asp
        835                 840                 845

Trp Glu Thr Gly Arg Ile Met Pro Asn Asn Tyr Lys Asn Gly Ser Asp
        850                 855                 860

Asp Gly Val Leu Ala Tyr Lys Leu Leu Val Gln Thr Gly Ser Arg Asp
865                 870                 875                 880

Lys Pro Ile Asp Ile Ser Gln Leu Thr Lys Gln Arg Leu Val Asp Ala
                885                 890                 895

Asp Gly Ile Ile Asn Pro Ser Ala Phe Tyr Ile Tyr Leu Thr Ala Trp
                900                 905                 910

Val Ser Asn Asp Pro Val Ala Tyr Ala Ala Ser Gln Ala Asn Ile Arg
                915                 920                 925

Pro His Arg Pro Glu Trp Val His Asp Lys Ala Asp Tyr Met Pro Glu
                930                 935                 940

Thr Arg Leu Arg Ile Pro Ala Ala Glu Pro Ile Glu Tyr Ala Gln Phe
945                 950                 955                 960

Pro Phe Tyr Leu Asn Gly Leu Arg Asp Thr Ser Asp Phe Val Glu Ala
                965                 970                 975

Ile Glu Lys Val Arg Val Ile Cys Asn Asn Tyr Thr Ser Leu Gly Leu
                980                 985                 990

Ser Ser Tyr Pro Asn Gly Tyr Pro Phe Leu Phe Trp Glu Gln Tyr Ile
                995                 1000                1005

Ser Leu Arg His Trp Leu Leu Leu Ser Ile Ser Val Val Leu Ala Cys
                1010                1015                1020

Thr Phe Leu Val Cys Ala Val Phe Leu Leu Asn Pro Trp Thr Ala Gly
1025                1030                1035                1040

Ile Ile Val Met Val Leu Ala Leu Met Thr Val Glu Leu Phe Gly Met
                1045                1050                1055

Met Gly Leu Ile Gly Ile Lys Leu Ser Ala Val Pro Val Val Ile Leu
                1060                1065                1070

Ile Ala Ser Val Gly Ile Gly Val Glu Phe Thr Val His Val Ala Leu
                1075                1080                1085

Ala Phe Leu Thr Ala Ile Gly Asp Lys Asn His Arg Ala Met Leu Ala
                1090                1095                1100

Leu Glu His Met Phe Ala Pro Val Leu Asp Gly Ala Val Ser Thr Leu
1105                1110                1115                1120

Leu Gly Val Leu Met Leu Ala Gly Ser Glu Phe Asp Phe Ile Val Arg
                1125                1130                1135

Tyr Phe Phe Ala Val Leu Ala Ile Leu Thr Val Leu Gly Val Leu Asn
                1140                1145                1150

Gly Leu Val Leu Leu Pro Val Leu Leu Ser Phe Phe Gly Pro Cys Pro
                1155                1160                1165

Glu Val Ser Pro Ala Asn Gly Leu Asn Arg Leu Pro Thr Pro Ser Pro
                1170                1175                1180

Glu Pro Pro Pro Ser Val Val Arg Phe Ala Val Pro Pro Gly His Thr
1185                1190                1195                1200

Asn Asn Gly Ser Asp Ser Ser Asp Ser Glu Tyr Ser Ser Gln Thr Thr
                1205                1210                1215

Val Ser Gly Ile Ser Glu Glu Leu Arg Gln Tyr Glu Ala Gln Gln Gly
                1220                1225                1230

-continued

```
Ala Gly Gly Pro Ala His Gln Val Ile Val Glu Ala Thr Glu Asn Pro
        1235                1240                1245
Val Phe Ala Arg Ser Thr Val Val His Pro Asp Ser Arg His Gln Pro
1250                1255                1260
Pro Leu Thr Pro Arg Gln Gln Pro His Leu Asp Ser Gly Ser Leu Ser
1265                1270                1275                1280
Pro Gly Arg Gln Gly Gln Gln Pro Arg Arg Asp Pro Arg Glu Gly
        1285                1290                1295
Leu Arg Pro Pro Pro Tyr Arg Pro Arg Arg Asp Ala Phe Glu Ile Ser
        1300                1305                1310
Thr Glu Gly His Ser Gly Pro Ser Asn Arg Asp Arg Ser Gly Pro Arg
        1315                1320                1325
Gly Ala Arg Ser His Asn Pro Arg Asn Pro Thr Ser Thr Ala Met Gly
        1330                1335                1340
Ser Ser Val Pro Ser Tyr Cys Gln Pro Ile Thr Thr Val Thr Ala Ser
1345                1350                1355                1360
Ala Ser Val Thr Val Ala Val His Pro Pro Gly Pro Gly Arg Asn
        1365                1370                1375
Pro Arg Gly Gly Pro Cys Pro Gly Tyr Glu Ser Tyr Pro Glu Thr Asp
        1380                1385                1390
His Gly Val Phe Glu Asp Pro His Val Pro Phe His Val Arg Cys Glu
        1395                1400                1405
Arg Arg Asp Ser Lys Val Glu Val Ile Glu Leu Gln Asp Val Glu Cys
        1410                1415                1420
Glu Glu Arg Pro Trp Gly Ser Ser Ser Asn
1425                1430

(2) INFORMATION FOR SEQ ID NO: 11:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 11:

Ile Ile Thr Pro Leu Asp Cys Phe Trp Glu Gly
1               5                   10

(2) INFORMATION FOR SEQ ID NO: 12:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 12:

Leu Ile Val Gly Gly
1               5

(2) INFORMATION FOR SEQ ID NO: 13:

(i) SEQUENCE CHARACTERISTICS:
        (A) LENGTH: 7 amino acids
        (B) TYPE: amino acid
        (C) STRANDEDNESS: single
        (D) TOPOLOGY: linear
```

(ii) MOLECULE TYPE: peptide (xi) SEQUENCE DESCRIPTION: SEQ ID NO: 13:

Pro Phe Phe Trp Glu Gln Tyr
1               5

(2) INFORMATION FOR SEQ ID NO: 14:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer"

(xi) SEQUENCE DESCRIPTION: SEQ ID NO: 14:

GGACGAATTC AARGTNCAYC ARYTNTGG                                               28

(2) INFORMATION FOR SEQ ID NO: 15:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer"

(xi) SEQUENCE DESCRIPTION: SEQ ID NO: 15:

GGACGAATTC CYTCCCARAA RCANTC                                                 26

(2) INFORMATION FOR SEQ ID NO: 16:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer"

(xi) SEQUENCE DESCRIPTION: SEQ ID NO: 16:

GGACGAATTC YTNGANTGYT TYTGGGA                                                27

(2) INFORMATION FOR SEQ ID NO: 17:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer"

(xi) SEQUENCE DESCRIPTION: SEQ ID NO: 17:

CATACCAGCC AAGCTTGTCN GGCCARTGCA T                                           31

(2) INFORMATION FOR SEQ ID NO: 18:

(i) SEQUENCE CHARACTERISTICS:
            (A) LENGTH: 5288 base pairs
            (B) TYPE: nucleic acid
            (C) STRANDEDNESS: single (D) TOPOLOGY: linear (ii) MOLECULE TYPE: cDNA (xi) SEQUENCE DESCRIPTION: SEQ ID NO: 18:

```
GAATTCCGGG GACCGCAAGG AGTGCCGCGG AAGCGCCCGA AGGACAGGCT CGCTCGGCGC      60
GCCGGCTCTC GCTCTTCCGC GAACTGGATG TGGGCAGCGG CGGCCGCAGA GACCTCGGGA     120
CCCCCGCGCA ATGTGGCAAT GGAAGGCGCA GGGTCTGACT CCCCGGCAGC GGCCGCGGCC     180
GCAGCGGCAG CAGCGCCCGC CGTGTGAGCA GCAGCAGCGG CTGGTCTGTC AACCGGAGCC     240
CGAGCCCGAG CAGCCTGCGG CCAGCAGCGT CCTCGCAAGC CGAGCGCCCA GGCGCGCCAG     300
GAGCCCGCAG CAGCGGCAGC AGCGCGCCGG GCCGCCCGGG AAGCCTCCGT CCCCGCGGCG     360
GCGGCGGCGG CGGCGGCGGC AACATGGCCT CGGCTGGTAA CGCCGCCGAG CCCCAGGACC     420
GCGGCGGCGG CGGCAGCGGC TGTATCGGTG CCCCGGGACG GCCGGCTGGA GGCGGGAGGC     480
GCAGACGGAC GGGGGGGCTG CGCCGTGCTG CCGCGCCGGA CCGGGACTAT CTGCACCGGC     540
CCAGCTACTG CGACGCCGCC TTCGCTCTGG AGCAGATTTC CAAGGGGAAG GCTACTGGCC     600
GGAAAGCGCC ACTGTGGCTG AGAGCGAAGT TTCAGAGACT CTTATTTAAA CTGGGTTGTT     660
ACATTCAAAA AAACTGCGGC AAGTTCTTGG TTGTGGGCCT CCTCATATTT GGGGCCTTCG     720
CGGTGGGATT AAAAGCAGCG AACCTCGAGA CCAACGTGGA GGAGCTGTGG GTGGAAGTTG     780
GAGGACGAGT AAGTCGTGAA TTAAATTATA CTCGCCAGAA GATTGGAGAA GAGGCTATGT     840
TTAATCCTCA ACTCATGATA CAGACCCCTA AGAAGAAGG TGCTAATGTC CTGACCACAG     900
AAGCGCTCCT ACAACACCTG GACTCGGCAC TCCAGGCCAG CCGTGTCCAT GTATACATGT     960
ACAACAGGCA GTGGAAATTG GAACATTTGT GTTACAAATC AGGAGAGCTT ATCACAGAAA    1020
CAGGTTACAT GGATCAGATA ATAGAATATC TTTACCCTTG TTTGATTATT ACACCTTTGG    1080
ACTGCTTCTG GGAAGGGGCG AAATTACAGT CTGGGACAGC ATACCTCCTA GGTAAACCTC    1140
CTTTGCGGTG GACAAACTTC GACCCTTTGG AATTCCTGGA AGAGTTAAAG AAAATAAACT    1200
ATCAAGTGGA CAGCTGGGAG GAAATGCTGA ATAAGGCTGA GGTTGGTCAT GGTTACATGG    1260
ACCGCCCCTG CCTCAATCCG GCCGATCCAG ACTGCCCCGC CACAGCCCCC AACAAAAATT    1320
CAACCAAACC TCTTGATATG GCCCTTGTTT TGAATGGTGG ATGTCATGGC TTATCCAGAA    1380
AGTATATGCA CTGGCAGGAG GAGTTGATTG TGGGTGGCAC AGTCAAGAAC AGCACTGGAA    1440
AACTCGTCAG CGCCCATGCC CTGCAGACCA TGTTCCAGTT AATGACTCCC AAGCAAATGT    1500
ACGAGCACTT CAAGGGGTAC GAGTATGTCT CACACATCAA CTGGAACGAG GACAAAGCGG    1560
CAGCCATCCT GGAGGCCTGG CAGAGGACAT ATGTGGAGGT GGTTCATCAG AGTGTCGCAC    1620
AGAACTCCAC TCAAAAGGTG CTTTCCTTCA CCACCACGAC CCTGGACGAC ATCCTGAAAT    1680
CCTTCTCTGA CGTCAGTGTC ATCCGCGTGG CCAGCGGCTA CTTACTCATG CTCGCCTATG    1740
CCTGTCTAAC CATGCTGCGC TGGGACTGCT CCAAGTCCCA GGGTGCCGTG GGGCTGGCTG    1800
GCGTCCTGCT GGTTGCACTG TCAGTGGCTG CAGGACTGGG CCTGTGCTCA TTGATCGGAA    1860
TTTCCTTTAA CGCTGCAACA ACTCAGGTTT TGCCATTTCT CGCTCTTGGT GTTGGTGTGG    1920
ATGATGTTTT TCTTCTGGCC CACGCCTTCA GTGAAACAGG ACAGAATAAA AGAATCCCTT    1980
TTGAGGACAC GACCGGGGAG TGCCTGAAGC GCACAGGAGC CAGCGTGGCC CTCACGTCCA    2040
TCAGCAATGT CACAGCCTTC TTCATGGCCG CGTTAATCCC AATTCCCGCT CTGCGGGCGT    2100
TCTCCCTCCA GGCAGCGGTA GTAGTGGTGT TCAATTTTGC CATGGTTCTG CTCATTTTTC    2160
CTGCAATTCT CAGCATGGAT TTATATCGAC GCGAGGACAG GAGACTGGAT ATTTTCTGCT    2220
```

```
GTTTTACAAG CCCCTGCGTC AGCAGAGTGA TTCAGGTTGA ACCTCAGGCC TACACCGACA    2280

CACACGACAA TACCCGCTAC AGCCCCCCAC CTCCCTACAG CAGCCACAGC TTTGCCCATG    2340

AAACGCAGAT TACCATGCAG TCCACTGTCC AGCTCCGCAC GGAGTACGAC CCCCACACGC    2400

ACGTGTACTA CACCACCGCT GAGCCGCGCT CCGAGATCTC TGTGCAGCCC GTCACCGTGA    2460

CACAGGACAC CCTCAGCTGC CAGAGCCCAG AGAGCACCAG CTCCACAAGG GACCTGCTCT    2520

CCCAGTTCTC CGACTCCAGC CTCCACTGCC TCGAGCCCCC CTGTACGAAG TGGACACTCT    2580

CATCTTTTGC TGAGAAGCAC TATGCTCCTT TCCTCTTGAA ACCAAAAGCC AAGGTAGTGG    2640

TGATCTTCCT TTTTCTGGGC TTGCTGGGGG TCAGCCTTTA TGGCACCACC CGAGTGAGAG    2700

ACGGGCTGGA CCTTACGGAC ATTGTACCTC GGGAAACCAG AGAATATGAC TTTATTGCTG    2760

CACAATTCAA ATACTTTTCT TTCTACAACA TGTATATAGT CACCCAGAAA GCAGACTACC    2820

CGAATATCCA GCACTTACTT TACGACCTAC ACAGGAGTTT CAGTAACGTG AAGTATGTCA    2880

TGTTGGAAGA AAACAAACAG CTTCCCAAAA TGTGGCTGCA CTACTTCAGA GACTGGCTTC    2940

AGGGACTTCA GGATGCATTT ACAGTGACT GGGAAACCGG GAAAATCATG CCAAACAATT    3000

ACAAGAATGG ATCAGACGAT GGAGTCCTTG CCTACAAACT CCTGGTGCAA ACCGGCAGCC    3060

GCGATAAGCC CATCGACATC AGCCAGTTGA CTAAACAGCG TCTGGTGGAT GCAGATGGCA    3120

TCATTAATCC CAGCGCTTTC TACATCTACC TGACGGCTTG GGTCAGCAAC GACCCCGTCG    3180

CGTATGCTGC CTCCCAGGCC AACATCCGGC CACACCGACC AGAATGGGTC CACGACAAAG    3240

CCGACTACAT GCCTGAAACA AGGCTGAGAA TCCCGGCAGC AGAGCCCATC GAGTATGCCC    3300

AGTTCCCTTT CTACCTCAAC GGGTTGCGGG ACACCTCAGA CTTTGTGGAG GCAATTGAAA    3360

AAGTAAGGAC CATCTGCAGC AACTATACGA GCCTGGGGCT GTCCAGTTAC CCCAACGGCT    3420

ACCCCTTCCT CTTCTGGGAG CAGTACATCG GCCTCCGCCA CTGGCTGCTG CTGTTCATCA    3480

GCGTGGTGTT GGCCTGCACA TTCCTCGTGT GCGCTGTCTT CCTTCTGAAC CCCTGGACGG    3540

CCGGGATCAT TGTGATGGTC CTGGCGCTGA TGACGGTCGA GCTGTTCGGC ATGATGGGCC    3600

TCATCGGAAT CAAGCTCAGT GCCGTGCCCG TGGTCATCCT GATCGCTTCT GTTGGCATAG    3660

GAGTGGAGTT CACCGTTCAC GTTGCTTTGG CCTTTCTGAC GGCCATCGGC GACAAGAACC    3720

GCAGGGCTGT GCTTGCCCTG GAGCACATGT TTGCACCCGT CCTGGATGGC GCCGTGTCCA    3780

CTCTGCTGGG AGTGCTGATG CTGGCGGGAT CTGAGTTCGA CTTCATTGTC AGGTATTTCT    3840

TTGCTGTGCT GGCGATCCTC ACCATCCTCG GCGTTCTCAA TGGGCTGGTT TTGCTTCCCG    3900

TGCTTTTGTC TTTCTTTGGA CCATATCCTG AGGTGTCTCC AGCCAACGGC TTGAACCGCC    3960

TGCCCACACC CTCCCCTGAG CCACCCCCA GCGTGGTCCG CTTCGCCATG CCGCCCGGCC    4020

ACACGCACAG CGGGTCTGAT TCCTCCGACT CGGAGTATAG TTCCCAGACG ACAGTGTCAG    4080

GCCTCAGCGA GGAGCTTCGG CACTACGAGG CCCAGCAGGG CGCGGGAGGC CCTGCCCACC    4140

AAGTGATCGT GGAAGCCACA GAAAACCCCG TCTTCGCCCA CTCCACTGTG GTCCATCCCG    4200

AATCCAGGCA TCACCCACCC TCGAACCCGA GACAGCAGCC CCACCTGGAC TCAGGGTCCC    4260

TGCCTCCCGG ACGGCAAGGC CAGCAGCCCC GCAGGGACCC CCCAGAGAA GGCTTGTGGC    4320

CACCCCTCTA CAGACCGCGC AGAGACGCTT TTGAAATTTC TACTGAAGGG CATTCTGGCC    4380

CTAGCAATAG GGCCCGCTGG GGCCCTCGCG GGCCCGTTC TCACAACCCT CGGAACCCAG    4440

CGTCCACTGC CATGGGCAGC TCCGTGCCCG GCTACTGCCA GCCATCACC ACTGTGACGG    4500

CTTCTGCCTC CGTGACTGTC GCCGTGCACC CGCCGCCTGT CCCTGGGCCT GGGCGGAACC    4560
```

-continued

```
CCCGAGGGGG ACTCTGCCCA GGCTACCCTG AGACTGACCA CGGCCTGTTT GAGGACCCCC    4620

ACGTGCCTTT CCACGTCCGG TGTGAGAGGA GGGATTCGAA GGTGGAAGTC ATTGAGCTGC    4680

AGGACGTGGA ATGCGAGGAG AGGCCCCGGG GAAGCAGCTC CAACTGAGGG TGATTAAAAT    4740

CTGAAGCAAA GAGGCCAAAG ATTGGAAACC CCCCACCCCC ACCTCTTTCC AGAACTGCTT    4800

GAAGAGAACT GGTTGGAGTT ATGGAAAAGA TGCCCTGTGC CAGGACAGCA GTTCATTGTT    4860

ACTGTAACCG ATTGTATTAT TTTGTTAAAT ATTTCTATAA ATATTTAAGA GATGTACACA    4920

TGTGTAATAT AGGAAGGAAG GATGTAAAGT GGTATGATCT GGGCTTCTC CACTCCTGCC     4980

CCAGAGTGTG GAGGCCACAG TGGGGCCTCT CCGTATTTGT GCATTGGGCT CCGTGCCACA    5040

ACCAAGCTTC ATTAGTCTTA AATTTCAGCA TATGTTGCTG CTGCTTAAAT ATTGTATAAT    5100

TTACTTGTAT AATTCTATGC AAATATTGCT TATGTAATAG GATTATTTTG TAAAGGTTTC    5160

TGTTTAAAAT ATTTTAAATT TGCATATCAC AACCCTGTGG TAGTATGAAA TGTTACTGTT    5220

AACTTTCAAA CACGCTATGC GTGATAATTT TTTTGTTTAA TGAGCAGATA TGAAGAAAGC    5280

CCGGAATT                                                           5288
```

(2) INFORMATION FOR SEQ ID NO: 19:

(i) SEQUENCE CHARACTERISTICS:
        (A) LENGTH: 1447 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 19:

```
Met Ala Ser Ala Gly Asn Ala Ala Glu Pro Gln Asp Arg Gly Gly
1               5                   10                  15

Gly Ser Gly Cys Ile Gly Ala Pro Gly Arg Pro Ala Gly Gly Arg
                20                  25                  30

Arg Arg Arg Thr Gly Gly Leu Arg Arg Ala Ala Ala Pro Asp Arg Asp
            35                  40                  45

Tyr Leu His Arg Pro Ser Tyr Cys Asp Ala Ala Phe Ala Leu Glu Gln
        50                  55                  60

Ile Ser Lys Gly Lys Ala Thr Gly Arg Lys Ala Pro Leu Trp Leu Arg
65                  70                  75                  80

Ala Lys Phe Gln Arg Leu Leu Phe Lys Leu Gly Cys Tyr Ile Gln Lys
                85                  90                  95

Asn Cys Gly Lys Phe Leu Val Val Gly Leu Leu Ile Phe Gly Ala Phe
                100                 105                 110

Ala Val Gly Leu Lys Ala Ala Asn Leu Glu Thr Asn Val Glu Glu Leu
            115                 120                 125

Trp Val Glu Val Gly Gly Arg Val Ser Arg Glu Leu Asn Tyr Thr Arg
130                 135                 140

Gln Lys Ile Gly Glu Glu Ala Met Phe Asn Pro Gln Leu Met Ile Gln
145                 150                 155                 160

Thr Pro Lys Glu Glu Gly Ala Asn Val Leu Thr Thr Glu Ala Leu Leu
                165                 170                 175

Gln His Leu Asp Ser Ala Leu Gln Ala Ser Arg Val His Val Tyr Met
            180                 185                 190

Tyr Asn Arg Gln Trp Lys Leu Glu His Leu Cys Tyr Lys Ser Gly Glu
        195                 200                 205

Leu Ile Thr Glu Thr Gly Tyr Met Asp Gln Ile Ile Glu Tyr Leu Tyr
```

-continued

```
            210                 215                 220
Pro Cys Leu Ile Ile Thr Pro Leu Asp Cys Phe Trp Glu Gly Ala Lys
225                 230                 235                 240

Leu Gln Ser Gly Thr Ala Tyr Leu Leu Gly Lys Pro Pro Leu Arg Trp
                245                 250                 255

Thr Asn Phe Asp Pro Leu Glu Phe Leu Glu Glu Leu Lys Lys Ile Asn
                260                 265                 270

Tyr Gln Val Asp Ser Trp Glu Glu Met Leu Asn Lys Ala Glu Val Gly
                275                 280                 285

His Gly Tyr Met Asp Arg Pro Cys Leu Asn Pro Ala Asp Pro Asp Cys
                290                 295                 300

Pro Ala Thr Ala Pro Asn Lys Asn Ser Thr Lys Pro Leu Asp Met Ala
305                 310                 315                 320

Leu Val Leu Asn Gly Gly Cys His Gly Leu Ser Arg Lys Tyr Met His
                325                 330                 335

Trp Gln Glu Glu Leu Ile Val Gly Gly Thr Val Lys Asn Ser Thr Gly
                340                 345                 350

Lys Leu Val Ser Ala His Ala Leu Gln Thr Met Phe Gln Leu Met Thr
                355                 360                 365

Pro Lys Gln Met Tyr Glu His Phe Lys Gly Tyr Glu Tyr Val Ser His
                370                 375                 380

Ile Asn Trp Asn Glu Asp Lys Ala Ala Ala Ile Leu Glu Ala Trp Gln
385                 390                 395                 400

Arg Thr Tyr Val Glu Val Val His Gln Ser Val Ala Gln Asn Ser Thr
                405                 410                 415

Gln Lys Val Leu Ser Phe Thr Thr Thr Leu Asp Asp Ile Leu Lys
                420                 425                 430

Ser Phe Ser Asp Val Ser Val Ile Arg Val Ala Ser Gly Tyr Leu Leu
                435                 440                 445

Met Leu Ala Tyr Ala Cys Leu Thr Met Leu Arg Trp Asp Cys Ser Lys
                450                 455                 460

Ser Gln Gly Ala Val Gly Leu Ala Gly Val Leu Leu Val Ala Leu Ser
465                 470                 475                 480

Val Ala Ala Gly Leu Gly Leu Cys Ser Leu Ile Gly Ile Ser Phe Asn
                485                 490                 495

Ala Ala Thr Thr Gln Val Leu Pro Phe Leu Ala Leu Gly Val Gly Val
                500                 505                 510

Asp Asp Val Phe Leu Leu Ala His Ala Phe Ser Glu Thr Gly Gln Asn
                515                 520                 525

Lys Arg Ile Pro Phe Glu Asp Arg Thr Gly Glu Cys Leu Lys Arg Thr
                530                 535                 540

Gly Ala Ser Val Ala Leu Thr Ser Ile Ser Asn Val Thr Ala Phe Phe
545                 550                 555                 560

Met Ala Ala Leu Ile Pro Ile Pro Ala Leu Arg Ala Phe Ser Leu Gln
                565                 570                 575

Ala Ala Val Val Val Phe Asn Phe Ala Met Val Leu Leu Ile Phe
                580                 585                 590

Pro Ala Ile Leu Ser Met Asp Leu Tyr Arg Arg Glu Asp Arg Arg Leu
                595                 600                 605

Asp Ile Phe Cys Cys Phe Thr Ser Pro Cys Val Ser Arg Val Ile Gln
                610                 615                 620

Val Glu Pro Gln Ala Tyr Thr Asp Thr His Asp Asn Thr Arg Tyr Ser
625                 630                 635                 640
```

-continued

```
Pro Pro Pro Pro Tyr Ser Ser His Ser Phe Ala His Glu Thr Gln Ile
            645                 650                 655
Thr Met Gln Ser Thr Val Gln Leu Arg Thr Glu Tyr Asp Pro His Thr
        660                 665                 670
His Val Tyr Tyr Thr Thr Ala Glu Pro Arg Ser Glu Ile Ser Val Gln
        675                 680                 685
Pro Val Thr Val Thr Gln Asp Thr Leu Ser Cys Gln Ser Pro Glu Ser
    690                 695                 700
Thr Ser Ser Thr Arg Asp Leu Leu Ser Gln Phe Ser Asp Ser Ser Leu
705                 710                 715                 720
His Cys Leu Glu Pro Pro Cys Thr Lys Trp Thr Leu Ser Ser Phe Ala
                725                 730                 735
Glu Lys His Tyr Ala Pro Phe Leu Leu Lys Pro Lys Ala Lys Val Val
            740                 745                 750
Val Ile Phe Leu Phe Leu Gly Leu Leu Gly Val Ser Leu Tyr Gly Thr
        755                 760                 765
Thr Arg Val Arg Asp Gly Leu Asp Leu Thr Asp Ile Val Pro Arg Glu
    770                 775                 780
Thr Arg Glu Tyr Asp Phe Ile Ala Ala Gln Phe Lys Tyr Phe Ser Phe
785                 790                 795                 800
Tyr Asn Met Tyr Ile Val Thr Gln Lys Ala Asp Tyr Pro Asn Ile Gln
                805                 810                 815
His Leu Leu Tyr Asp Leu His Arg Ser Phe Ser Asn Val Lys Tyr Val
            820                 825                 830
Met Leu Glu Glu Asn Lys Gln Leu Pro Lys Met Trp Leu His Tyr Phe
        835                 840                 845
Arg Asp Trp Leu Gln Gly Leu Gln Asp Ala Phe Asp Ser Asp Trp Glu
    850                 855                 860
Thr Gly Lys Ile Met Pro Asn Asn Tyr Lys Asn Gly Ser Asp Asp Gly
865                 870                 875                 880
Val Leu Ala Tyr Lys Leu Leu Val Gln Thr Gly Ser Arg Asp Lys Pro
                885                 890                 895
Ile Asp Ile Ser Gln Leu Thr Lys Gln Arg Leu Val Asp Ala Asp Gly
            900                 905                 910
Ile Ile Asn Pro Ser Ala Phe Tyr Ile Tyr Leu Thr Ala Trp Val Ser
        915                 920                 925
Asn Asp Pro Val Ala Tyr Ala Ala Ser Gln Ala Asn Ile Arg Pro His
    930                 935                 940
Arg Pro Glu Trp Val His Asp Lys Ala Asp Tyr Met Pro Glu Thr Arg
945                 950                 955                 960
Leu Arg Ile Pro Ala Ala Glu Pro Ile Glu Tyr Ala Gln Phe Pro Phe
                965                 970                 975
Tyr Leu Asn Gly Leu Arg Asp Thr Ser Asp Phe Val Glu Ala Ile Glu
            980                 985                 990
Lys Val Arg Thr Ile Cys Ser Asn Tyr Thr Ser Leu Gly Leu Ser Ser
        995                 1000                1005
Tyr Pro Asn Gly Tyr Pro Phe Leu Phe Trp Glu Gln Tyr Ile Gly Leu
    1010                1015                1020
Arg His Trp Leu Leu Leu Phe Ile Ser Val Val Leu Ala Cys Thr Phe
1025                1030                1035                1040
Leu Val Cys Ala Val Phe Leu Leu Asn Pro Trp Thr Ala Gly Ile Ile
                1045                1050                1055
```

```
Val Met Val Leu Ala Leu Met Thr Val Glu Leu Phe Gly Met Met Gly
             1060                1065                1070

Leu Ile Gly Ile Lys Leu Ser Ala Val Pro Val Val Ile Leu Ile Ala
        1075                1080                1085

Ser Val Gly Ile Gly Val Glu Phe Thr Val His Val Ala Leu Ala Phe
   1090                1095                1100

Leu Thr Ala Ile Gly Asp Lys Asn Arg Arg Ala Val Leu Ala Leu Glu
1105                1110                1115                1120

His Met Phe Ala Pro Val Leu Asp Gly Ala Val Ser Thr Leu Leu Gly
             1125                1130                1135

Val Leu Met Leu Ala Gly Ser Glu Phe Asp Phe Ile Val Arg Tyr Phe
             1140                1145                1150

Phe Ala Val Leu Ala Ile Leu Thr Ile Leu Gly Val Leu Asn Gly Leu
             1155                1160                1165

Val Leu Leu Pro Val Leu Leu Ser Phe Phe Gly Pro Tyr Pro Glu Val
             1170                1175                1180

Ser Pro Ala Asn Gly Leu Asn Arg Leu Pro Thr Pro Ser Pro Glu Pro
1185                1190                1195                1200

Pro Pro Ser Val Val Arg Phe Ala Met Pro Pro Gly His Thr His Ser
             1205                1210                1215

Gly Ser Asp Ser Ser Asp Ser Glu Tyr Ser Ser Gln Thr Thr Val Ser
             1220                1225                1230

Gly Leu Ser Glu Glu Leu Arg His Tyr Glu Ala Gln Gln Gly Ala Gly
             1235                1240                1245

Gly Pro Ala His Gln Val Ile Val Glu Ala Thr Glu Asn Pro Val Phe
             1250                1255                1260

Ala His Ser Thr Val Val His Pro Glu Ser Arg His His Pro Pro Ser
1265                1270                1275                1280

Asn Pro Arg Gln Gln Pro His Leu Asp Ser Gly Ser Leu Pro Pro Gly
             1285                1290                1295

Arg Gln Gly Gln Gln Pro Arg Arg Asp Pro Pro Arg Glu Gly Leu Trp
             1300                1305                1310

Pro Pro Leu Tyr Arg Pro Arg Arg Asp Ala Phe Glu Ile Ser Thr Glu
             1315                1320                1325

Gly His Ser Gly Pro Ser Asn Arg Ala Arg Trp Gly Pro Arg Gly Ala
             1330                1335                1340

Arg Ser His Asn Pro Arg Asn Pro Ala Ser Thr Ala Met Gly Ser Ser
1345                1350                1355                1360

Val Pro Gly Tyr Cys Gln Pro Ile Thr Thr Val Thr Ala Ser Ala Ser
             1365                1370                1375

Val Thr Val Ala Val His Pro Pro Val Pro Gly Pro Gly Arg Asn
             1380                1385                1390

Pro Arg Gly Gly Leu Cys Pro Gly Tyr Pro Glu Thr Asp His Gly Leu
             1395                1400                1405

Phe Glu Asp Pro His Val Pro Phe His Val Arg Cys Glu Arg Arg Asp
             1410                1415                1420

Ser Lys Val Glu Val Ile Glu Leu Gln Asp Val Glu Cys Glu Glu Arg
1425                1430                1435                1440

Pro Arg Gly Ser Ser Ser Asn
             1445
```

PATCHED GENES AND USES RELATED THERETO

CROSS REFERENCE TO RELATED APPLICATIONS

This application is a continuation of application Ser. No. 08/954,668, filed Oct. 20, 1997 and issuing as U.S. Pat. No. 6,172,200 on Jan. 9, 2001, which is a continuation of application Ser. No. 08/540,406, filed Oct. 6, 1995 and issuing as U.S. Pat. No. 5,837,538 on Nov. 17, 1998, which is a continuation-in-part of application Ser. No. 08/319,745, filed on Oct. 7, 1994 and now abandoned, the disclosures of all of which are incorporated by reference and to which priority is claimed under 35 U.S.C. §120.

INTRODUCTION

1. Technical Field

The field of this invention concerns segment polarity genes and their uses.

2. Background

Segment polarity genes were discovered in flies as mutations which change the pattern of structures of the body segments. Mutations in the genes cause animals to develop the changed patterns on the surfaces of body segments, the changes affecting the pattern along the head to tail axis. For example, mutations in the gene patched cause each body segment to develop without the normal structures in the center of each segment. In their stead is a mirror image of the pattern normally found in the anterior segment. Thus cells in the center of the segment make the wrong structures, and point them in the wrong direction with reference to the over all head-to-tail polarity of the animal. About sixteen genes in the class are known. The encoded proteins include kinases, transcription factors, a cell junction protein, two secreted proteins called wingless (WG) and hedgehog (HH), a single transmembrane protein called patched (PTC), and some novel proteins not related to any known protein. All of these proteins are believed to work together in signaling pathways that inform cells about their neighbors in order to set cell fates and polarities.

Many of the segment polarity proteins of *Drosophila* and other invertebrates are closely related to vertebrate proteins, implying that the molecular mechanisms involved are ancient. Among the vertebrate proteins related to the fly genes are En-1 and -2, which act in vertebrate brain development and WNT-1, which is also involved in brain development, but was first found as the oncogene implicated in many cases of mouse breast cancer. In flies, the patched gene is transcribed into RNA in a complex and dynamic pattern in embryos, including fine transverse stripes in each body segment primordium. The encoded protein is predicted to contain many transmembrane domains. It has no significant similarity to any other known protein. Other proteins having large numbers of transmembrane domains include a variety of membrane receptors, channels through membranes and transporters through membranes.

The hedgehog (HH) protein of flies has been shown to have at least three vertebrate relatives: Sonic hedgehog (Shh); Indian hedgehog, and Desert hedgehog. The Shh is expressed in a group of cells at the posterior of each developing limb bud. This is exactly the same group of cells found to have an important role in signaling polarity to the developing limb. The signal appears to be graded, with cells close to the posterior source of the signal forming posterior digits and other limb structures and cells farther from the signal source forming more anterior structures. It has been known for many years that transplantation of the signaling cells, a region of the limb bud known as the "zone of polarizing activity (ZPA)" has dramatic effects on limb patterning. Implanting a second ZPA anterior to the limb bud causes a limb to develop with posterior features replacing the anterior ones (in essence little fingers instead of thumbs). Shh has been found to be the long sought ZPA signal. Cultured cells making Shh protein (SHH), when implanted into the anterior limb bud region, have the same effect as an implanted ZPA. This establishes that Shh is clearly a critical trigger of posterior limb development.

The factor in the ZPA has been thought for some time to be related to another important developmental signal that polarizes the developing spinal cord. The notochord, a rod of mesoderm that runs along the dorsal side of early vertebrate embryos, is a signal source that polarizes the neural tube along the dorsal-ventral axis. The signal causes the part of the neural tube nearest to the notochord to form floor plate, a morphologically distinct part of the neural tube. The floor plate, in turn, sends out signals to the more dorsal parts of the neural tube to further determine cell fates. The ZPA was reported to have the same signaling effect as the notochord when transplanted to be adjacent to the neural tube, suggesting the ZPA makes the same signal as the notochord. In keeping with this view, Shh was found to be produced by notochord cells and floor plate cells. Tests of extra expression of Shh in mice led to the finding of extra expression of floor plate genes in cells which would not normally turn them on. Therefore Shh appears to be a component of the signal from notochord to floor plate and from floor plate to more dorsal parts of the neural tube. Besides limb and neural tubes, vertebrate hedgehog genes are also expressed in many other tissues including, but not limited to the peripheral nervous system, brain, lung, liver, kidney, tooth primordia, genitalia, and hindgut and foregut endoderm.

PTC has been proposed as a receptor for HH protein based on genetic experiments in flies. A model for the relationship is that PTC acts through a largely unknown pathway to inactivate both its own transcription and the transcription of the wingless segment polarity gene. This model proposes that HH protein, secreted from adjacent cells, binds to the PTC receptor, inactivates it, and thereby prevents PTC from turning off its own transcription or that of wingless. A number of experiments have shown coordinate events between PTC and HH.

Relevant Literature

Descriptions of patched, by itself or its role with hedgehog may be found in Hooper and Scott, Cell 59, 751–765 (1989); Nakano et al., Nature, 341, 508–513 (1989) (both of which also describes the sequence for *Drosophila* patched) Simcox et al., Development 107, 715–722 (1989); Hidalgo and Ingham, Development, 110, 291–301 (1990); Phillips et al., Development, 110, 105–114 (1990); Sampedro and Guerrero, Nature 353, 187–190 (1991); Ingham et al., Nature 353, 184–187 (1991); and Taylor et al., Mechanisms of Development 42, 89–96 (1993). Discussions of the role of hedgehog include Riddle et al., Cell 75, 1401–1416 (1993); Echelard et al., Cell 75, 1417–1430 (1993); Krauss et al., Cell 75, 1431–1444 (1993); Tabata and Kornberg, Cell 76, 89–102 (1994); Heemskerk & DiNardo, Cell 76, 449–460 (1994); Relink et al., Cell 76, 761–775 (1994); and a short review article by Ingham, Current Biology 4, 347–350 (1994). The sequence for the *Drosophila* 5' non-coding region was reported to the GenBank, accession number M28418, referred to in Hooper and Scott (1989), supra. See also, Forbes, et al., Development 1993 Supplement 115–124.

SUMMARY OF THE INVENTION

Methods for isolating patched genes, particularly mammalian patched genes, including the mouse and human patched genes, as well as invertebrate patched genes and sequences, are provided. The methods include identification of patched genes from other species, as well as members of the same family of proteins. The subject genes provide methods for producing the patched protein, where the genes and proteins may be used as probes for research, diagnosis, binding of hedgehog protein for its isolation and purification, gene therapy, as well as other utilities.

DESCRIPTION OF THE SPECIFIC EMBODIMENTS

Figure 1:
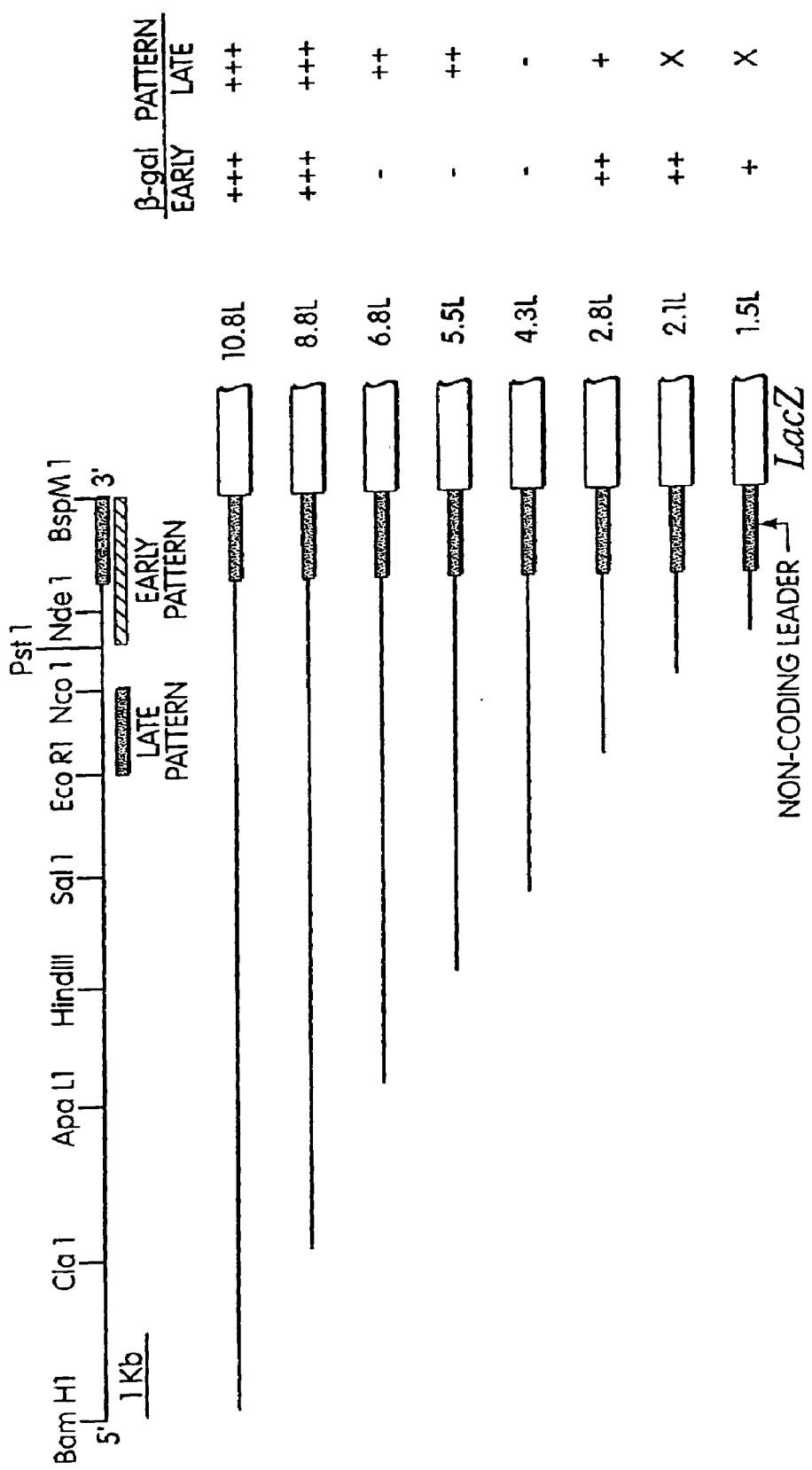
FIG. 1 is a graph having a restriction map of about 10 kbp of the 5' region upstream from the initiation codon of *Drosophila* patched gene and bar graphs of constructs of truncated portions of the 5' region joined to β-galactosidase, where the constructs are introduced into fly cell lines for the production of embryos. The expression of β-gal in the embryos is indicated in the right-hand table during early and late development of the embryo. The greater the number of +'s, the more intense the staining.

Methods are provided for identifying members of the patched (ptc) gene family from invertebrate and vertebrate, e.g. mammalian, species, as well as the entire cDNA sequence of the mouse and human patched gene. Also, sequences for invertebrate patched genes are provided. The patched gene encodes a transmembrane protein having a large number of transmembrane sequences.

In identifying the mouse and human patched genes, primers were employed to move through the evolutionary tree from the known *Drosophila* ptc sequence. Two primers are employed from the *Drosophila* sequence with appropriate restriction enzyme linkers to amplify portions of genomic DNA of a related invertebrate, such as mosquito. The sequences are selected from regions which are not likely to diverge over evolutionary time and are of low degeneracy. Conveniently, the regions are the N-terminal proximal sequence, generally within the first 1.5 kb, usually within the first 1 kb, of the coding portion of the cDNA, conveniently in the first hydrophilic loop of the protein. Employing the polymerase chain reaction (PCR) with the primers, a band can be obtained from mosquito genomic DNA. The band may then be amplified and used in turn as a probe. One may use this probe to probe a cDNA library from an organism in a different branch of the evolutionary tree, such as a butterfly. By screening the library and identifying sequences which hybridize to the probe, a portion of the butterfly patched gene may be obtained. One or more of the resulting clones may then be used to rescreen the library to obtain an extended sequence, up to and including the entire coding region, as well as the non-coding 5'- and 3'-sequences. As appropriate, one may sequence all or a portion of the resulting cDNA coding sequence.

One may then screen a genomic or cDNA library of a species higher in the evolutionary scale with appropriate probes from one or both of the prior sequences. Of particular interest is screening a genomic library, of a distantly related invertebrate, e.g. beetle, where one may use a combination of the sequences obtained from the previous two species, in this case, the *Drosophila* and the butterfly. By appropriate techniques, one may identify specific clones which bind to the probes, which may then be screened for cross hybridization with each of the probes individually. The resulting fragments may then be amplified, e.g. by subcloning.

By having all or parts of the 4 different patched genes, in the presently illustrated example, *Drosophila* (fly), mosquito, butterfly and beetle, one can now compare the patched genes for conserved sequences. Cells from an appropriate mammalian limb bud or other cells expressing patched, such as notochord, neural tube, gut, lung buds, or other tissue, particularly fetal tissue, may be employed for screening. Alternatively, adult tissue which produces patched may be employed for screening. Based on the consensus sequence available from the 4 other species, one can develop probes where at each site at least 2 of the sequences have the same nucleotide and where the site varies that each species has a unique nucleotide, inosine may be used, which binds to all 4 nucleotides.

Either PCR may be employed using primers or, if desired, a genomic library from an appropriate source may be probed. With PCR, one may use a cDNA library or use reverse transcriptase-PCR (RT-PCR), where mRNA is available from the tissue. Usually, where fetal tissue is employed, one will employ tissue from the first or second trimester, preferably the latter half of the first trimester or the second trimester, depending upon the particular host. The age and source of tissue will depend to a significant degree on the ability to surgically isolate the tissue based on its size, the level of expression of patched in the cells of the tissue, the accessibility of the tissue, the number of cells expressing patched and the like. The amount of tissue available should be large enough so as to provide for a sufficient amount of mRNA to be usefully transcribed and amplified. With mouse tissue, limb bud of from about 10 to 15 dpc (days post conception) may be employed.

In the primers, the complementary binding sequence will usually be at least 14 nucleotides, preferably at least about 17 nucleotides and usually not more than about 30 nucleotides. The primers may also include a restriction enzyme sequence for isolation and cloning. With RT-PCR, the mRNA may be enriched in accordance with known ways, reverse transcribed, followed by amplification with the appropriate primers. (Procedures employed for molecular cloning may be found in Molecular Cloning: A Laboratory Manual, Sambrook et al., eds., Cold Spring Harbor Laboratories, Cold Spring Harbor, N.Y., 1988). Particularly, the primers may conveniently come from the N-terminal proximal sequence or other conserved region, such as those sequences where at least five amino acids are conserved out of eight amino acids in three of the four sequences. This is illustrated by the sequences (SEQ ID NO:11) IITPLDCFWEG, (SEQ ID NO:12) LIVGG, and (SEQ ID NO:13) PFFWEQY. Resulting PCR products of expected size are subcloned and may be sequenced if desired.

The cloned PCR fragment may then be used as a probe to screen a cDNA library of mammalian tissue cells expressing patched, where hybridizing clones may be isolated under appropriate conditions of stringency. Again, the cDNA library should come from tissue which expresses patched, which tissue will come within the limitations previously described. Clones which hybridize may be subcloned and rescreened. The hybridizing subclones may then be isolated and sequenced or may be further analyzed by employing RNA blots and in situ hybridizations in whole and sectioned embryos. Conveniently, a fragment of from about 0.5 to 1 kbp of the N-terminal coding region may be employed for the Northern blot.

The mammalian gene may be sequenced and as described above, conserved regions identified and used as primers for investigating other species. The N-terminal proximal region, the C-terminal region or an intermediate region may be employed for the sequences, where the sequences will be selected having minimum degeneracy and the desired level of conservation over the probe sequence.

The DNA sequence encoding PTC may be cDNA or genomic DNA or fragment thereof, particularly complete exons from the genomic DNA, may be isolated as the sequence substantially free of wild-type sequence from the chromosome, may be a 50 kbp fragment or smaller fragment, may be joined to heterologous or foreign DNA, which may be a single nucleotide, oligonucleotide of up to 50 bp, which may be a restriction site or other identifying DNA for use as a primer, probe or the like, or a nucleic acid of greater than 50 bp, where the nucleic acid may be a portion of a cloning or expression vector, comprise the regulatory regions of an expression cassette, or the like. The DNA may be isolated, purified being substantially free of proteins and other nucleic acids, be in solution, or the like.

The subject gene may be employed for producing all or portions of the patched protein. The subject gene or fragment thereof, generally a fragment of at least 12 bp, usually at least 18 bp, may be introduced into an appropriate vector for extrachromosomal maintenance or for integration into the host. Fragments will usually be immediately joined at the 5' and/or 3' terminus to a nucleotide or sequence not found in the natural or wild-type gene, or joined to a label other than a nucleic acid sequence. For expression, an expression cassette may be employed, providing for a transcriptional and translational initiation region, which may be inducible or constitutive, the coding region under the transcriptional control of the transcriptional initiation region, and a transcriptional and translational termination region. Various transcriptional initiation regions may be employed which are functional in the expression host. The peptide may be expressed in prokaryotes or eukaryotes in accordance with conventional ways, depending upon the purpose for expression. For large production of the protein, a unicellular organism or cells of a higher organism, e.g. eukaryotes such as vertebrates, particularly mammals, may be used as the expression host, such as $E.\ coli,\ B,\ subtilis,\ S.\ cerevisiae$, and the like. In many situations, it may be desirable to express the patched gene in a mammalian host, whereby the patched gene will be transported to the cellular membrane for various studies. The protein has two parts which provide for a total of six transmembrane regions, with a total of six extracellular loops, three for each part. The character of the protein has similarity to a transporter protein. The protein has two conserved glycosylation signal triads.

The subject nucleic acid sequences may be modified for a number of purposes, particularly where they will be used intracellularly, for example, by being joined to a nucleic acid cleaving agent, e.g. a chelated metal ion, such as iron or chromium for cleavage of the gene; as an antisense sequence; or the like. Modifications may include replacing oxygen of the phosphate esters with sulfur or nitrogen, replacing the phosphate with phosphoramide, etc.

With the availability of the protein in large amounts by employing an expression host, the protein may be isolated and purified in accordance with conventional ways. A lysate may be prepared of the expression host and the lysate purified using HPLC, exclusion chromatography, gel electrophoresis, affinity chromatography, or other purification technique. The purified protein will generally be at least about 80% pure, preferably at least about 90% pure, and may be up to 100% pure. By pure is intended free of other proteins, as well as cellular debris.

The polypeptide may be used for the production of antibodies, where short fragments provide for antibodies specific for the particular polypeptide, whereas larger fragments or the entire gene allow for the production of antibodies over the surface of the polypeptide or protein, where the protein may be in its natural conformation.

Antibodies may be prepared in accordance with conventional ways, where the expressed polypeptide or protein may be used as an immunogen, by itself or conjugated to known immunogenic carriers, e.g. KLH, pre-S HBsAg, other viral or eukaryotic proteins, or the like. Various adjuvants may be employed, with a series of injections, as appropriate. For monoclonal antibodies, after one or more booster injections, the spleen may be isolated, the splenocytes immortalized, and then screened for high affinity antibody binding. The immortalized cells, e.g. hybridomas, producing the desired antibodies may then be expanded. For further description, see Monoclonal Antibodies: A Laboratory Manual, Harlow and Lane eds., Cold Spring Harbor Laboratories, Cold Spring Harbor, N.Y., 1988. If desired, the mRNA encoding the heavy and light chains may be isolated and mutigenized by cloning in $E.\ coli$, and the heavy and light chains may be mixed to further enhance the affinity of the antibody. The antibodies may find use in diagnostic assays for detection of the presence of the PTC protein on the surface of cells or to inhibit the transduction of signal by the PTC protein ligand by competing for the binding site.

The mouse patched gene (SEQ ID NO:09) encodes a protein (SEQ ID NO:10) which has about 38% identical amino acids to fly PTC (SEQ ID NO:6) over about 1,200 amino acids. This amount of conservation is dispersed through much of the protein excepting the C-terminal region. The mouse protein also has a 50 amino acid insert relative to the fly protein. The human patched gene (SEQ ID NO:18) contains an open reading fram of about 1450 amino acids (SEQ ID NO:19) that is about 96% identical (98% similar) to mouse ptc (SEQ ID NO:09). The human patched gene (SEQ ID NO:18), including coding and non-coding sequences, is about 89% identical to the mouse patched gene (SEQ ID NO:09).

The butterfly PTC homolog (SEQ ID NO:4) is 1,300 amino acids long and overall has a 50% amino acid identity (72% similarity) to fly PTC (SEQ ID NO:6). With the exception of a divergent C-terminus, this homology is evenly spread across the coding sequence. A 267 bp exon from the beetle patched gene encodes an 89 amino acid protein fragment which was found to be 44% and 51% identical to the corresponding regions of fly and butterfly PTC respectively.

The mouse ptc message is about 8 kb long and the message is present in low levels as early as 7 dpc, the abundancy increasing by 11 and 15 dpc. Northern blot indicates a clear decrease in the amount of message at 17 dpc. In the adult, PTC RNA is present in high amounts in the brain and lung, as well as in moderate amounts in the kidney and liver. Weak signals are detected in heart, spleen, skeletal muscle and testes.

In mouse embryos, ptc mRNA is present at 7 dpc, using in situ hybridization. ptc is present at high levels along the neural axis of 8.5 dpc embryos. By 11.5 dpc, ptc can be detected in developing lung buds and gut, consistent with its Northern profile. In addition, the gene is present at high levels in the ventricular zone of the central nervous system as well as in the zona limitans of the prosencephalon. ptc is also strongly transcribed in the perichondrium condensing cartilage of 11.5 and 13.5 dpc limb buds, as well as in the ventral portion of the somites, a region which is prospective sclerotome and eventually forms bone in the vertebral column. PTC is present in a wide range of tissues from endodermal, mesodermal, as well as ectodermal origin, evidencing the fundamental role in many aspects of embryonic development, including the condensation of cartilage, the patterning of limbs, the differentiation of lung tissue, and the generation of neurons.

The patched nucleic acid may be used for isolating the gene from various mammalian sources of interest, particularly primate, more particularly human, or from domestic animals, both pet and farm, e.g. lagomorpha, rodentiae, porcine, bovine, feline, canine, ovine, equine, etc. By using probes, particularly labeled probes of DNA sequences, of the patched gene, one may be able to isolate mRNA or genomic DNA, which may be then used for identifying mutations, particularly associated with genetic diseases, such as spina bifida, limb defects, lung defects, problems with tooth development, liver and kidney development, peripheral nervous system development, and other sites where a patched gene is involved in regulation. The subject probes can also be used for identifying the level of expression in cells associated with the testis to determine the relationship with the level of expression and sperm production.

The gene or fragments thereof may be used as probes for identifying the 5' non-coding region comprising the transcriptional initiation region, particularly the enhancer regulating the transcription of patched. By probing a genomic library, particularly with a probe comprising the 5' coding region, one can obtain fragments comprising the 5' non-coding region. If necessary, one may walk the fragment to obtain further 5' sequence to ensure that one has at least a functional portion of the enhancer. It is found that the enhancer is proximal to the 5' coding region, a portion being in the transcribed sequence and downstream from the promoter sequences. The transcriptional initiation region may be used for many purposes, studying embryonic development, providing for regulated expression of patched protein or other protein of interest during embryonic development or thereafter, and in gene therapy.

The gene may also be used for gene therapy, by transfection of the normal gene into embryonic stem cells or into mature cells. A wide variety of viral vectors can be employed for transfection and stable integration of the gene into the genome of the cells. Alternatively, micro-injection may be employed, fusion, or the like for introduction of genes into a suitable host cell. See, for example, Dhawan et al., Science 254, 1509–1512 (1991) and Smith et al., Molecular and Cellular Biology (1990) 3268–3271.

By providing for the production of large amounts of PTC protein, one can use the protein for identifying ligands which bind to the PTC protein. Particularly, one may produce the protein in cells and employ the polysomes in columns for isolating ligands for the PTC protein. One may incorporate the PTC protein into liposomes by combining the protein with appropriate lipid surfactants, e.g. phospholipids, cholesterol, etc., and sonicate the mixture of the PTC protein and the surfactants in an aqueous medium. With one or more established ligands, e.g. hedgehog, one may use the PTC protein to screen for antagonists which inhibit the binding of the ligand. In this way, drugs may be identified which can prevent the transduction of signals by the PTC protein in normal or abnormal cells.

The PTC protein, particularly binding fragments thereof, the gene encoding the protein, or fragments thereof, particularly fragments of at least about 18 nucleotides, frequently of at least about 30 nucleotides and up to the entire gene, more particularly sequences associated with the hydrophilic loops, may be employed in a wide variety of assays. In these situations, the particular molecules will normally be joined to another molecule, serving as a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin etc. For the specific binding members, the complementary member would normally be labeled with a molecule which provides for detection, in accordance with known procedures. The assays may be used for detecting the presence of molecules which bind to the patched gene or PTC protein, in isolating molecules which bind to the patched gene, for measuring the amount of patched, either as the protein or the message, for identifying molecules which may serve as agonists or antagonists, or the like.

Various formats may be used in the assays. For example, mammalian or invertebrate cells may be designed where the cells respond when an agonist binds to PTC in the membrane of the cell. An expression cassette may be introduced into the cell, where the transcriptional initiation region of patched is joined to a marker gene, such as $\beta$-galactosidase, for which a substrate forming a blue dye is available. A 1.5 kb fragment that responds to PTC signaling has been identified and shown to regulate expression of a heterologous gene during embryonic development. When an agonist binds to the PTC protein, the cell will turn blue. By employing a competition between an agonist and a compound of interest, absence of blue color formation will indicate the presence of an antagonist. These assays are well known in the literature. Instead of cells, one may use the protein in a membrane environment and determine binding affinities of compounds. The PTC may be bound to a surface and a labeled ligand for PTC employed. A number of labels have been indicated previously. The candidate compound is added with the labeled ligand in an appropriate buffered medium to the surface bound PTC. After an incubation to ensure that binding has occurred, the surface may be washed free of any non-specifically bound components of the assay medium, particularly any non-specifically bound labeled ligand, and any label bound to the surface determined. Where the label is an enzyme, substrate producing a detectable product may be used. The label may be detected and measured. By using standards, the binding affinity of the candidate compound may be determined.

The availability of the gene and the protein allows for investigation of the development of the fetus and the role patched and other molecules play in such development. By employing antisense sequences of the patched gene, where the sequences may be introduced in cells in culture, or a vector providing for transcription of the antisense of the patched gene introduced into the cells, one can investigate the role the PTC protein plays in the cellular development. By providing for the PTC protein or fragment thereof in a soluble form which can compete with the normal cellular PTC protein for ligand, one can inhibit the binding of ligands to the cellular PTC protein to see the effect of variation in concentration of ligands for the PTC protein on the cellular development of the host. Antibodies against PTC can also be used to block function, since PTC is exposed on the cell surface.

The subject gene may also be used for preparing transgenic laboratory animals, which may serve to investigate embryonic development and the role the PTC protein plays in such development. By providing for variation in the expression of the PTC protein, employing different transcriptional initiation regions which may be constitutive or inducible, one can determine the developmental effect of the differences in PTC protein levels. Alternatively, one can use the DNA to knock out the PTC protein in embryonic stem cells, so as to produce hosts with only a single functional patched gene or where the host lacks a functional patched gene. By employing homologous recombination, one can introduce a patched gene, which is differentially regulated, for example, is expressed to the development of the fetus, but not in the adult. One may also provide for expression of the patched gene in cells or tissues where it is not normally expressed or at abnormal times of development. One may provide for mis-expression or failure of expression in certain tissue to mimic a human disease. Thus, mouse models of spina bifida or abnormal motor neuron differentiation in the developing spinal cord are made available. In addition, by providing expression of PTC protein in cells in which it is otherwise not normally produced, one can induce changes in cell behavior upon binding of ligand to the PTC protein.

Areas of investigation may include the development of cancer treatments. The wingless gene, whose transcription is regulated in flies by PTC, is closely related to a mammalian oncogene, Wnt-1, a key factor in many cases of mouse breast cancer. Other Wnt family members, which are secreted signaling proteins, are implicated in many aspects of development. In flies, the signaling factor decapentaplegic, a member of the TGF-beta family of signaling proteins, known to affect growth and development in mammals, is also controlled by PTC. Since members of both the TGF-beta and Wnt families are expressed in mice in places close to overlapping with patched, the common regulation provides an opportunity in treating cancer. Also, for repair and regeneration, proliferation competent cells making PTC protein can find use to promote regeneration and healing for damaged tissue, which tissue may be regenerated by transfecting cells of damaged tissue with the ptc gene and its normal transcription initiation region or a modified transcription initiation region. For example, PTC may be useful to stimulate growth of new teeth by engineering cells of the gums or other tissues where PTC protein was during an earlier developmental stage or is expressed.

Since Northern blot analysis indicates that ptc is present at high levels in adult lung tissue, the regulation of ptc expression or binding to its natural ligand may serve to inhibit proliferation of cancerous lung cells. The availability of the gene encoding PTC and the expression of the gene allows for the development of agonists and antagonists. In addition, PTC is central to the ability of neurons to differentiate early in development. The availability of the gene allows for the introduction of PTC into host diseased tissue, stimulating the fetal program of division and/or differentiation. This could be done in conjunction with other genes which provide for the ligands which regulate PTC activity or by providing for agonists other than the natural ligand.

The availability of the coding region for various ptc genes from various species, allows for the isolation of the 5' non-coding region comprising the promoter and enhancer associated with the ptc genes, so as to provide transcriptional and post-transcriptional regulation of the ptc gene or other genes, which allow for regulation of genes in relation to the regulation of the ptc gene. Since the ptc gene is autoregulated, activation of the ptc gene will result in activation of transcription of a gene under the transcriptional control of the transcriptional initiation region of the ptc gene. The transcriptional initiation region may be obtained from any host species and introduced into a heterologous host species, where such initiation region is functional to the desired degree in the foreign host. For example, a fragment of from about 1.5 kb upstream from the initiation codon, up to about 10 kb, preferably up to about 5 kb may be used to provide for transcriptional initiation regulated by the PTC protein, particularly the *Drosophila* 5'-non-coding region (GenBank accession no. M28418).

The following examples are offered by illustration not by way of limitation.

EXPERIMENTAL

Methods and Materials

I. PCR on Mosquito (*Anopheles gambiae*) Genomic DNA:

PCR primers were based on amino acid stretches of fly PTC that were not likely to diverge over evolutionary time and were of low degeneracy. Two such primers (P2R1 (SEQ ID NO:14): GGACGAATTCAARGTNCAYCA-RYTNTGG, P4R1: (SEQ ID NO:15) GGACGAATTCCYTCCCARAARCANTC, (the underlined sequences are Eco RI linkers) amplified an appropriately sized band from mosquito genomic DNA using the PCR. The program conditions were as follows:

94° C. 4 min.; 72° C. Add Taq;
[49° C. 30 sec.; 72° C. 90 sec.; 94° C. 15 sec] 3 times
[94° C. 15 sec.; 50° C. 30 sec.; 72° C. 90 sec] 35 times
72° C. 10 min; 4° C. hold This band was subcloned into the EcoRV site of pBluescript II and sequenced using the USB Sequence kit.

II. Screen of a Butterfly cDNA Library with Mosquito PCR Product

Using the mosquito PCR product (SEQ ID NO:7) as a probe, a 3 day embryonic *Precis coenia* λgt10 cDNA library (generously provided by Sean Carroll) was screened. Filters were hybridized at 65° C. overnight in a solution containing 5×SSC, 10% dextran sulfate, 5×Denhardt's, 200 μg/ml sonicated salmon sperm DNA, and 0.5% SDS. Filters were washed in 0.1×SSC, 0.1% SDS at room temperature several times to remove nonspecific hybridization. Of the 100,000 plaques initially screened, 2 overlapping clones, L1 and L2, were isolated, which corresponded to the N terminus of butterfly PTC. Using L2 as a probe, the library filters were rescreened and 3 additional clones (L5, L7, L8) were isolated which encompassed the remainder of the ptc coding sequence. The full length sequence of butterfly ptc (SEQ ID NO:3) was determined by ABI automated sequencing.

III. Screen of a *Tribolium* (beetle) Genomic Library with Mosquito PCR Product and 900 bp Fragment from the Butterfly Clone A λgem11 genomic library from *Tribolium casteneum* (gift of Rob Dennell) was probed with a mixture of the mosquito PCR (SEQ ID NO:7) product and BstXI/EcoRI fragment of L2. Filters were hybridized at 55° C. overnight and washed as above. Of the 75,000 plaques screened, 14 clones were identified and the SacI fragment of T8 (SEQ ID NO:1), which crosshybridized with the mosquito and butterfly probes, was subcloned into pBluescript.

IV. PCR on Mouse cDNA Using Degenerate Primers Derived from Regions Conserved in the Four Insect Homologues Two degenerate PCR primers (P4REV: (SEQ ID NO:16) GGACGAATTCYTNGANTGYTTYTGGGA; P22: (SEQ ID NO:17) CATACCAGCCAAGCTTGTCIGGCC-ARTGCAT) were designed based on a comparison of PTC amino acid sequences from fly (*Drosophila melanogaster*) (SEQ ID NO:6), mosquito (*Anopheles gambiae*)(SEQ ID NO:8), butterfly (*Precis coenia*)(SEQ ID NO:4), and beetle (*Tribolium casteneum*)(SEQ ID NO:2). I represents inosine, which can form base pairs with all four nucleotides. P22 was used to reverse transcribe RNA from 12.5 dpc mouse limb bud (gift from David Kingsley) for 90 min at 37° C. PCR using P4REV(SEQ ID NO:17) and P22(SEQ ID NO:18) was then performed on 1 µl of the resultant cDNA under the following conditions:

94° C. 4 min.; 72° C. Add Taq;

[94° C. 15 sec.; 50° C. 30 sec.; 72° C. 90 sec.] 35 times

72° C. 10 min.; 4° C. hold

PCR products of the expected size were subcloned into the TA vector (Invitrogen) and sequenced with the Sequenase Version 2.0 DNA Sequencing Kit (U.S.B.).

Using the cloned mouse PCR fragment as a probe, 300,000 plaques of a mouse 8.5 dpc λgt10 cDNA library (a gift from Brigid Hogan) were screened at 65° C. as above and washed in 2×SSC, 0.1% SDS at room temperature. 7 clones were isolated, and three (M2 M4, and M8) were subcloned into pBluescript II. 200,000 plaques of this library were rescreened using first, a 1.1 kb EcoRI fragment from M2 to identify 6 clones (M9–M16) and secondly a mixed probe containing the most N terminal (XhoI fragment from M2) and most C terminal sequences (BamHI/BglII fragment from M9) to isolate 5 clones (M17–M21). M9, M10, M14, and M17–21 were subcloned into the EcoRI site of pBluescript II (Strategene).

V. RNA Blots and in situ Hybridizations in Whole and Sectioned Mouse Embryos Northerns:

A mouse embryonic Northern blot and an adult multiple tissue Northern blot (obtained from Clontech) were probed with a 900 bp EcoRI fragment from an N terminal coding region of mouse ptc. Hybridization was performed at 65° C. in 5×SSPE, 10×Denhardt's, 100 µg/ml sonicated salmon sperm DNA, and 2% SDS. After several short room temperature washes in 2×SSC, 0.05% SDS, the blots were washed at high stringency in 0.1×SSC, 0.1% SDS at 50C.

In situ hybridization of sections:

7.75, 8.5, 11.5, and 13.5 dpc mouse embryos were dissected in PBS and frozen in Tissue-Tek medium at –80° C. 12–16 µm frozen sections were cut, collected onto Vecta-Bond (Vector Laboratories) coated slides, and dried for 30–60 minutes at room temperature. After a 10 minute fixation in 4% paraformaldehyde in PBS, the slides were washed 3 times for 3 minutes in PBS, acetylated for 10 minutes in 0.25% acetic anhydride in triethanolamine, and washed three more times for 5 minutes in PBS. Prehybridization (50% formamide, 5×SSC, 250 µg/ml yeast tRNA, 500 µg/ml sonicated salmon sperm DNA, and 5×Denhardt's) was carried out for 6 hours at room temperature in 50% formamide/5×SSC humidified chambers. The probe, which consisted of 1 kb from the N-terminus of ptc, was added at a concentration of 200–1000 ng/ml into the same solution used for prehybridization, and then denatured for five minutes at 80° C. Approximately 75 µl of probe were added to each slide and covered with Parafilm. The slides were incubated overnight at 65° C. in the same humidified chamber used previously. The following day, the probe was washed successively in 5×SSC (5 minutes, 65° C.), 0.2×SSC (1 hour, 65° C.), and 0.2×SSC (10 minutes, room temperature). After five minutes in buffer B1 (0.1M maleic acid, 0.15 M NaCl, pH 7.5), the slides were blocked for 1 hour at room temperature in 1% blocking reagent (Boerhinger-Mannheim) in buffer B1, and then incubated for 4 hours in buffer B1 containing the DIG-AP conjugated antibody (Boerhinger-Mannheim) at a 1:5000 dilution. Excess antibody was removed during two 15 minute washes in buffer B1, followed by five minutes in buffer B3 (100 mM Tris, 100 mM NaCl, 5 mM $MgCl_2$, pH 9.5). The antibody was detected by adding an alkaline phosphatase substrate (350 µl 75 mg/ml X-phosphate in DMF, 450 µl 50 mg/ml NBT in 70% DMF in 100 mls of buffer B3) and allowing the reaction to proceed over-night in the dark. After a brief rinse in 10 mM Tris, 1 mM EDTA, pH 8.0, the slides were mounted with Aquamount (Lerner Laboratories).

VI. *Drosophila* 5-Transcriptional Initiation Region β-gal Constructs.

A series of constructs were designed that link different regions of the ptc promoter from *Drosophila* to a LacZ reporter gene in order to study the cis regulation of the ptc expression pattern. See FIG. 1. A 10.8 kb BamHI/BspM1 fragment comprising the 5'-non-coding region of the mRNA at its 3'-terminus was obtained and truncated by restriction enzyme digestion as shown in FIG. 1. These expression cassettes were introduced into *Drosophila* lines using a P-element vector (Thummel et al., Gene 74, 445–456 (1988), which were injected into embryos, providing flies which could be grown to produce embryos. (See Spradling and Rubin, Science (1982) 218, 341–347 for a description of the procedure.) The vector used a pUC8 background into which was introduced the white gene to provide for yellow eyes, portions of the P-element for integrtion, and the constructs were inserted into a polylinker upstream from the LacZ gene. The resulting embryos were stained using antibodies to LacZ protein conjugated to HRP and the embryos developed with OPD dye to identify the expression of the LacZ gene. The staining pattern is described in FIG. 1, indicating whether there was staining during the early and late development of the embryo.

VII. Isolation of a Mouse ptc Gene

Homologues of fly PTC (SEQ ID NO:6) were isolated from three insects: mosquito, butterfly and beetle, using either PCR or low stringency library screens. PCR primers to six amino acid stretches of PTC of low mutatability and degeneracy were designed. One primer pair, P2 and P4, amplified an homologous fragment of ptc from mosquito genomic DNA that corresponded to the first hydrophilic loop of the protein. The 345 bp PCR product (SEQ ID NO:7) was subcloned and sequenced and when aligned to fly PTC, showed 67% amino acid identity.

The cloned mosquito fragment was used to screen a butterfly λGT 10 cDNA library. Of 100,000 plaques screened, five overlapping clones were isolated and used to obtain the full length coding sequence. The butterfly PTC homologue (SEQ ID NO:4) is 1,311 amino acids long and overall has 50% amino acid identity (72% similarity) to fly PTC. With the exception of a divergent C-terminus, this homology is evenly spread across the coding sequence. The mosquito PCR clone (SEQ ID NO:7) and a corresponding fragment of butterfly cDNA were used to screen a beetle λgem11 genomic library. Of the plaques screened, 14 clones were identified. A fragment of one clone (T8), which hybridized with the original probes, was subcloned and sequenced. This 3 kb piece contains an 89 amino acid exon (SEQ ID NO:2) which is 44% and 51% identical to the corresponding regions of fly and butterfly PTC respectively.

Using an alignment of the four insect homologues in the first hydrophilic loop of the PTC, two PCR primers were designed to a five and six amino acid stretch which were identical and of low degeneracy. These primers were used to isolate the mouse homologue using RT-PCR on embryonic limb bud RNA. An appropriately sized band was amplified and upon cloning and sequencing, it was found to encode a protein 65% identical to fly PTC. Using the cloned PCR product and subsequently, fragments of mouse ptc cDNA, a mouse embryonic λcDNA library was screened. From about 300,000 plaques, 17 clones were identified and of these, 7 form overlapping cDNA's which comprise most of the protein-coding sequence (SEQ ID NO:9).

VIIa. Developmental and Tissue Distribution of Mouse PTC RNA

In both the embryonic and adult Northern blots, the ptc probe detects a single 8 kb message. Further exposure does not reveal any additional minor bands. Developmentally, ptc mRNA is present in low levels as early as 7 dpc and becomes quite abundant by 11 and 15 dpc. While the gene is still present at 17 dpc, the Northern blot indicates a clear decrease in the amount of message at this stage. In the adult, ptc RNA is present in high amounts in the brain and lung, as well as in moderate amounts in the kidney and liver. Weak signals are detected in heart, spleen, skeletal muscle, and testes.

VIIb. In situ Hybridization of Mouse PTC in Whole and Section Embryos

Northern analysis indicates that ptc mRNA is present at 7 dpc, while there is no detectable signal in sections from 7.75 dpc embryos. This discrepancy is explained by the low level of transcription. In contrast, ptc is present at high levels along the neural axis of 8.5 dpc embryos. By 11.5 dpc, ptc can be detected in the developing lung buds and gut, consistent with its adult Northern profile. In addition, the gene is present at high levels in the ventricular zone of the central nervous system, as well as in the zona limitans of the prosencephalon. ptc is also strongly transcribed in the condensing cartilage of 11.5 and 13.5 dpc limb buds, as well as in the ventral portion of the somites, a region which is prospective sclerotome and eventually forms bone in the vertebral column. ptc is present in a wide range of tissues from endodermal, mesodermal and ectodermal origin supporting its fundamental role in embryonic development.

VIII. Isolation of the Human ptc Gene

To isolate human ptc (hptc), $2 \times 10^5$ plaques from a human lung cDNA library (HL3022a, Clonetech) were screened with a 1 kbp mouse ptc fragment, M2-2. Filters were hybridized overnight at reduced stringency (60° C. in 5×SSC, 10% dextran sulfate, 5×Denhardt's, 0.2 mg/ml sonicated salmon sperm DNA, and 0.5% SDS). Two positive plaques (H1 and H2) were isolated, the inserts cloned into pBluescript, and upon sequencing, both contained sequence highly similar to the mouse ptc homolog. To isolate the 5' end, an additional $6 \times 10^5$ plaques were screened in duplicate with M2-3 EcoR I and M2-3 Xho I (containing 5' untranslated sequence of mouse ptc) probes. Ten plaques were purified and of these, 6 inserts were subloned into pBluescript. To obtain the full coding sequence, H2 was fully and H14, H20, and H21 were partially sequenced. The 5.1 kbp of human ptc sequence (SEQ ID NO:18) contains an open reading frame of 1447 amino acids (SEQ ID NO:19) that is 96% identical and 98% similar to mouse ptc. The 5' and 3' untranslated sequences of human ptc (SEQ ID NO:18) are also highly similar to mouse ptc (SEQ ID NO:09) suggesting conserved regulatory sequence.

IX. Comparison of Mouse, Human, Fly and Butterfly Sequences

The deduced mouse PTC protein sequence (SEQ ID NO:10) has about 38% identical amino acids to fly PTC over about 1,200 amino acids. This amount of conservation is dispersed through much of the protein excepting the C-terminal region. The mouse protein also has a 50 amino acid insert relative to the fly protein. Based on the sequence conservation of PTC and the functional conservation of hedgehog between fly and mouse, one concludes that ptc functions similarly in the two organisms. A comparison of the amino acid sequences of mouse (mptc) (SEQ ID NO:10), human (hptc) (SEQ ID NO:19), butterfly (bptc)(SEQ ID NO:4) and *drosophila* (ptc) (SEQ ID NO:6) is shown in Table 1.

TABLE 1 alignment of human, mouse, fly, and butterfly PTC homologs

```
alignment of human, mouse, fly, and butterfly ptc homologs
HPTC  MASAGNAAEPQDR--GGGGSGCIGAPGRPAGGGRRRRTGGLRRAAAPDRDYLHRPSYCDA
MPTC  MASAGNAA---------------GALGRQAGGGRRRRTGGPHRA-APDRDYLHRPSYCDA
PTC   M-----DRDSLPRVPDTHGD--VVDE---------KLFSDL---------YI-RTSWVDA
BPTC  MVAPDSEAPSNPRITAAHESPCATEA---------RHSADL---------YI-RTSWVDA
      *                           .  ..               *. *  * **

HPTC  AFALEQISKGKATGRKAPLWLRAKFQRLLFKLGCYIQKNCGKFLVVGLLIFGAFAVGLKA
MPTC  AFALEQISKGKATGRKAPLWLRAKFQRLLFKLGCYIQKNCGKFLVVGLLIFGAFAVGLKA
PTC   QVALDQIDKGKARGSRTAIYLRSVFQSHLETLGSSVQKHAGKVLFVAILVLSTFCVGLKS
BPTC  ALALSELEKGNIEGGRTSLWIRAWLQEQLFILGCFLQGDAGKVLFVAILVLSTFCVGLKS
      **  .. **.  *  ..... .*. .*   *  **  .* . ** * *...*.....* ****.

HPTC  ANLETNVEELWVEVGGRVSRELNYTRQKIGEEAMFNPQLMIQTPKEEGANVLTTEALLQH
MPTC  ANLETNVEELWVEVGGRVSRELNYTRQKIGEEAMFNPQLMIQTPKEEGANVLTTEALLQH
PTC   AQIHSKVHQLWIQEGGRLEAELAYTQKTIGEDESATHQLLIQTTHDPNASVLHPQALLAH
BPTC  AQIHTRVDQLWVQEGGRLEAELKYTAQALGEADSSTHQLVIQTAKDPDVSLLHPGALLEH
      *..... *..**.. ***.   ** **  . .**       **.***   .   ..*    *** *

HPTC  LDSALQASRVHVYMYNRQWKLEHLCYKSGELITET-GYMDQIIEYLYPCLIITPLDCFWE
MPTC  LDSALQASRVHVYMYNRQWKLEHLCYKSGELITET-GYMDQIIEYLYPCLIITPLDCFWE
PTC   LEVLVKATAVKVHLYDTEWGLRDMCNMPSTPSFEGIYYIEQILRHLIPCSIITPLDCFWE
BPTC  LKVVHAATRVTVHMYDIEWRLKDLCYSPSIPDFEGYHHIESIIDNVIPCAIITPLDCFWE
      *    *. * * .*.. .* *  ..*   ..     *     .. *.  . **  *********

HPTC  GAKLQSGTAYLLGKPPLR----WTNFDPLEFLEELK------KINYQVDSWEEMLNKAEV
MPTC  GAKLQSGTAYLLGKPPLR----WTNFDPLEFLEELK------KINYQVDSWEEMLNKAEV
PTC   GSQLL-GPESAVVIPGLNQRLLWTTLNPASVMQYMKQKMSEEKISFDFETVEQYNKRAAI
BPTC  GSKLL-GPDYPIYVPHLKHKLQWTHLNPLEVVEEVK-KL---KFQFPLSTIEAYMKRAGI
      *..*  *     . * *      ** ...*    .. .*        *. .   . *  ...* .

HPTC  GHGYMDRPCLNPADPDCPATAPNKNSTKPLDMALVLNGGCHGLSRKYMHWQEELIVGGTV
MPTC  GHGYMDRPCLNPADPDCPATAPNKNSTKPLDVALVLNGGCQGLSRKYMHWQEELIVGGTV
PTC   GSGYMEKPCLNPLNPNCPDTAPNKNSTQPPDVGAILSGGCYGYAAKHMRWPEELIVGGRK
BPTC  TSAYMKKPCLDPTDPHCPATAPNKKSGHIPDVAAELSHGCYGFAAAYMHWPEQLIVGGAT
      .**  .***.*  .*.**  *****.*      *... *. ** *  .   *** * *****
```

TABLE 1-continued alignment of human, mouse, fly, and butterfly PTC homologs

```
HPTC KNSTGKLVSAHALQTMFQLMTPKQMYEHFKGYEYVSHINWNEDKAAAILEAWQRTYVEVV
MPTC KNATGKLVSAHALQTMFQLMTPKQMYEHFRGYDYVSHINWNEDRAAAILEAWQRTYVEVV
PTC  RNRSGHLRKAQALQSVVQLMTEKEMYDQWQDNYKVHHLGWTQEKAAEVLNAWQRNFSREV
BPTC RNSTSALRSARALQTVVQLMGEREMYEYWADHYKVHQIGWNQEKAAAVLDAWQRKFAAEV
     .*  .. *  *.***.. ***   ..**.    .   * ..  * ...**.*.****.  .   *

HPTC HQSVAQNSTQK----VLSFTTTTLDDILKSFSDVSVIRVASGYLLMLAYACLTMLRW-DC
MPTC HQSVAPNSTQK----VLPFTTTTLDDILKSFSDVSVIRVASGYLLMLAYACLTMLRW-DC
PTC  EQLLRKQSRIATNYDIYVFSSAALDDILAKFSHPSALSIVIGVAVTVLYAFCTLLRWRDP
BPTC RKI-TTSGSVSSAYSFYPFSTSTLNDILGKFSEVSLKNIILGYMFMLIYVAVTLIQWRDP
      .       .       *.....*.***  **.  *   .  *   .  *  *...*  *

HPTC SKSQGAVGLAAGVLLVALSVAGLGLCSLIGISFMAATTQVLPFLALGVGVDDVFLLAHAF
MPTC SKSQGAVGLAGVLLVALSVAAGLGLCSLIGISFNAATTQVLPFLALGVGVDDVFLLAHAF
PTC  VRGQSSVGVAGVLLMCFSTAAGLGLSALLGIVFNAASTQVVPFLALGLGVDHIFMLTAAY
BPTC IRSQAGVGIAGVLLLSITVAAGLGFCALLGIPFNASSTQIVPFLALGLGVQDMFLLTHTY
     ..*..**.*****.  .. *****..*.*.** ***..**..******.**...*.*. ..

HPTC SETGQNKRIPFEDRTGECLKRTGASVALTSISNVTAFFMAALIPIPALRAFSLQAAVVVV
MPTC SETGQNKRIPFEDRTGECLKRTGASVALTSISNVTAFFMAALIPIPALRAFSLQAAVVVV
PTC  AESN------RREQTKLILKKVGPSILFSACSTAGSFFAAAFIPVPALKVFCLQAAIVMC
BPTC VEQAGD--VPREERTGLVLKKSGLSVLLASLCNVMAFLAAALLPIPAFRVFCLQAAILLL
        *       ..*    **. * *. ...   .*. **.*.**..  * ****.

HPTC FNFAMVLLIFPAILSMDLYRREDRRLDIFCCFTSPCVSRVIQVEPQAYTDTHDNTRYSPP
MPTC FNFAMVLLIFPAILSMDLYRREDRRLDIFCCFSFCVSRVIQVEPQAYTEPHSNTRYSPP
PTC  SNLAAALLVFPAMISLDLRRRTAGRADIFCCCF-PVWKEQPKVAPPVLPLNNNNGR----
BPTC FNLGSILLVFPAMISLDLRRRSAARADLLCCLM-P---ESP------LPKKKIPER----
     *..  **.****..*.** **   *  *...**     *              *

HPTC PPYSSHSFAHETQITMQSTVQLRTEYDPHTHVYYTTAEPRSEISVQPVTVTQDT LSCQSP
MPTC PPYTSHSFAHETHITMQSTVQLRTEYDPHTHVYYTTAEPRSEISVQPVTVTQDNLSCQSP
PTC  --------------------------------GARHPKSCNNNRVPLPAQNPLLEQRA
BPTC --------------------------------AKTRKNDKTHRID-TTRQPLDPDVS
                                       .  ..  .   ... *  . .

HPTC ESTSSTRDLLSQFSDSSLHCLEFPCTKWTLSSFAEKHYAPFLLKPKAKVVVIFLFLGLLG
MPTC ESTSSTRDLLSQFSDSSLHCLEPPCTKWTLSSFAEKHYAPFLLKPKAKVVVILLFLGLLG
PTC  DIPGSS-----------HSLASF----SLATFAFQHYTPFLMRSWVKFLTVMGFLAALI
BPTC ENVTKT-----------CCL-SV----SLTKWAKNQYAPFIMRPAVKVTSMLALIAVIL
       .    .          * .    .*. *  ...*.****   *     .   ....

HPTC VSLYGTTRVRDGLDLTDIVPRETREYDFIAAQFKYFSFYNMYIVTQKA-DYPNIQHLLYD
MPTC VSLYGTTRVRDGLDLTDIVPRETREYDFIAAQFKYFSFYNMYIVTQKA-DYPNIQHLLYD
PTC  SSLYASTRLQDGLDIIDLVPKDSNEHKFLDAQTRLFGFYSMYAVTQGNFEYPTQQQLLRD
BPTC TSVWGATKVKDGLDLTDIVPENTDEHEFLSRQEKYFGFYNMYAVTQGNFEYPTNQKLLYE
     *.  ..*...****.*.**..  *  *.    * .*.**.** ***  .** * **  .

HPTC LHRSFSNVKYVMLEENKQLPKMWLHYFRDWLQGLQDAFDSDWETGKIMPNN-YKNGSDDG
MPTC LHKSFSNVKYVMLEENKQLPQMWLHYFRDWLQGLQDAFDSDWZTGRIMPNN-YKNGSDDG
PTC  YHDSFVRVPHVIKNDNGGLPDFWLLLFSEWLGNLQKIFDEEYRDGRLTKECWFPNASSDA
BPTC YHDQFVRIPNIIKNDNGGLTKFWLSLFRDWLLDLQVAFDKEVASGCITQEYWCKNASDEG
      *  *   . ...* ** .** ** ***.** **.  *...*.  * .*

HPTC VLAYKLLVQTGSRDKPIDISQLTK-QRLVDADGIINPSAFYIYLTAWVSNDPVAYAASQA
MPTC VLAYKLLVQTGSRDKPIDISQLTK-QRLVDADGIINPSAFYIYLTAWVSNDPVAYAASQA
PTC  ILAYKLIVQTGHVDNPVDKELVLT-NRLVNSDGIINQRAFYNYLSAWATNDVEAYGASQG
BPTC ILAYKLMVQTGHVDNPIDKSLITAGHRLVDKDGIINPKAFYNYLSAWATNDALAYGASQG
     .*****.****  *.*.*   .     .***.*****  ***.**.**  ** **.***

HPTC NIRPHRPEWVHDKADYMPETRLRIPAAEPIEYAQFPFYLNGLRDTSDFVEAIEKVRTICS
MPTC NIRPHRPEWVHDKADYMPETRLRIPAAEPIEYAQFPFYLNGLRDTSDFVEAIEKVRVICN
PTC  KLYPEPRQYFHQPNEY----DLKIPKSLPLVYAQMPFYLHGLTDTSQIKTLIGEIRDLSV
BPTC NLKPQPQRWIHSPEDV----HLEIKKSSPLIYTQLPFYLSGLSDTDSIKTLIRSVRDLCL
     .. *.   *  ./////*  *  .  *.*  **** ** **     *    . *.  .

HPTC NYTSLGLSSYPNGYPFLFWEQYIGLRHWLLLFISVVLACTFLVCAVFLLNPWTAGIIVMV
MPTC NYTSLGLSSYPNGYPFLFWEQYISLRHWLLLSISVVLACTFLVCAVFLLNPWTAGIIVMV
PTC  KYEGFGLPNYPSGIPFIFWEQYMTLRSSLAMILACVLLAALVLVSLLLLSVWAAVLVILS
BPTC KYEAKGLPNFPSGIPFLFWEQYLYLRTSLLLALACALGAVFIAVMVLLLNAWAAVLVTLA
       .* . **...*.* **.*****. **   *  ..  *   .. ..**. *.* .. .

HPTC LALMVTELFGMMGLIGIKLSAVPVVILIASVGIGVEFTVHVALAFLTAIGDKNRRAVLAL
MPTC LALMVTELFGMMGLIGIKLSAVPVVILIASVGIGVEFTVHVALAFLTAIGDKNHRAMLAL
PTC  VLASLAQIFGAMTLLGIKLSAIPAVILILSVGMMLCFNVLISLGFMTSVGNRQRRVQLSM
BPTC LATLVLQLLGVMALLGVKLSAMPPVLLVLAIGRGVHFTVHLCLGFVTSIGCKRRRASLAL
```

TABLE 1-continued alignment of human, mouse, fly, and butterfly PTC homologs

```
          ...* * *.*.****.* ***. ...*   . * * . *.*.*..* . .*  *..

HPTC  EHMFAPVLDGAVSTLLGVLMLAGSEFDFIVRYFFAVLAILTILGVLNGLVLLPVLLSFFG
MPTC  EHMFAPVLDGAVSTLLGVLMLAGSEFDFIVRYFFAVLAILTVLGVLNGLVLLPVLLSFFG
PTC   QMSLGPLVHGMLTSGVAVFMLSTSPFEFVIRHFCWLLLVVLCVGACNSLLVFPILLSMVG
BPTC  ESVLAPVVHGALAAALAASMLAASEFGFVARLFLRLLLALVFLGLIDGLLFFPIVLSILG
         . ..*...*  ...  .. **. * * *. ** .*  .  .*  ...*. .*..**  *

HPTC  PYPEVSPANGLNRLPTPSPEPPPSVVRFAMPPGHTHSGSDSSDSEYSSQTTVSGLSE-EL
MPTC  PCPEVSPANGLNRLPTPSPEPPPSVYRFAVPPGHTNNGSDSSDSEYSSQTTVSGISE-EL
PTC   PEAELVPLEHPDRISTPSFLPVRSSKRSGKSYVVQGSRSSRGSCQKSNHHHHKDLNDPSL
BPTC  PAAEVRPIEHPERLSTPSPKCSPIHPRKSSSSSGGGDKSSRTS--KSAPRPC----APSL
       * .*. *  .  .*..****       *. .      *       *              *

HPTC  RHYEAQQGAGGPAHQVIVEATENPVFAHSTVVHPESRHHPPSNPRQQPHLDSGSLPPGRQ
MPTC  RQYEAQQGAGGPAHQVIVEATENPVFARSTVVHPDSRHQPPLTPRQQPHLDSGSLSPGRQ
PTC   TTITEEPQSWKSSNSSIQMFNDWTYQFREQ--RPASYAAPPPAYHKAAAQQHHQEQGPPT
BPTC  TTITEEPSSWHSSAHSVQSSMQSIVVQFEVVVETTTYNGSDSASGRSTPTKSSHGGAITT
              .  . ..   . . .              .  .          .

HPTC  GQQPRRDPPREGLWPPLYRPRRDAFEISTEGHSGPSNRARWGPRGARSHNPRNPASTAMG
MPTC  GQQPRRDPPREGLRPPPYRPRRDAFEISTEGHSGPSNRDRSGPRGARSHNPRNPTSTAMG
PTC   TPPPPFPTA----------------YPPELQSIVVQPEVTVETTHS----------DS
BPTC  TKVTATANIKVEVVTPSDRKSRRSYHYYDRRRDRDEDRDRDRERDRDRDRDRDRDRDRDR
                                              .    .

HPTC  SSVPGYCQPITTVTASASVTVAVHPPPVPGPGRNPRGGLCPGY---PETDHGLEEDPHVP
MPTC  SSVPSYCQPITTVTASASVTVAVHPP--PGPGRNPRGGFCFGYESYPETDHGVFEDPHVP
PTC   NT--------TKVTATANIKVELAMP-----GRAVRS---YNFTS---------------
BPTC  DR--------DRERSRERDRRDRYRD-----ERDHRA---SPRENGRDSGHE--------
                         .                    *  *.

HPTC  FHVRCERRDSKVEVIELQDVECEERPRGSSSN
MPTC  FHVRCERRDSKVEVIELQDVECEERPWGSSSN
PTC   --------------------------------
BFTC  --------------------------SDSSRH
```

The identity of ten other clones recovered from the mouse library is not determined. These cDNAs cross-hybridize with mouse ptc sequence, while differing as to their restriction maps. These genes encode a family of proteins related to the patched protein. Alignment of the human and mouse nucleotide sequences, which includes coding and noncoding sequence, reveals 89% identity.

In accordance with the subject invention, mammalian patched genes, including the mouse and human genes, are provided which allow for high level production of the patched protein, which can serve many purposes. The patched protein may be used in a screening for agonists and antagonists, for isolation of its ligand, particularly hedgehog, more particularly Sonic hedgehog, and for assaying for the transcription of the mRNA ptc. The protein or fragments thereof may be used to produce antibodies specific for the protein or specific epitopes of the protein. In addition, the gene may be employed for investigating embryonic development, by screening fetal tissue, preparing transgenic animals to serve as models, and the like.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of screening for compounds that bind to a patched protein, said method comprising:

(a) combining a candidate compound with a cell comprising an expression cassette further comprising (i) a transcriptional initiation region, (ii) a transcriptional termination region, and (iii) a nucleic acid sequence encoding the patched protein under the transcriptional regulation of said transcriptional initiation region and said transcriptional termination region, wherein said nucleic acid sequence (I) encodes the patched protein, which patched protein is present in the membrane of said cell and (II) hybridizes under stringent conditions, including a wash step of 0.2×SSC at 65° C., to the nucleic acid sequence represented in SEQ ID NO: 18, and wherein the patched protein can bind to a hedgehog polypeptide; and (b) assaying for the binding of said candidate compound to the patched protein.

2. The method of claim 1, wherein said cell is a mammalian cell.

3. The method of claim 1, wherein the patched protein is encoded by a nucleic acid sequence represented in SEQ ID NO: 18.

4. The method of claim 1, wherein the patched protein comprises an amino acid sequence represented in SEQ ID NO: 19.

* * * * *